United States Patent [19]

Pinschmidt, Jr. et al.

[11] Patent Number: 4,691,026
[45] Date of Patent: Sep. 1, 1987

[54] SELF- AND HYDROXYL REACTIVE FORMALDEHYDE-FREE CYCLIC HEMIAMIDAL AND HEMIAMIDE KETAL CROSSLINKING MONOMERS

[75] Inventors: Robert K. Pinschmidt, Jr., Allentown; Dale D. Dixon, Kutztown; William F. Burgoyne, Jr., Allentown, all of Pa.

[73] Assignee: Air Products and Chemicals, Inc., Allentown, Pa.

[21] Appl. No.: 760,442

[22] Filed: Jul. 30, 1985

[51] Int. Cl.$^4$ .................. C07D 207/12; C07D 251/18; C07D 251/46; C07D 251/70

[52] U.S. Cl. ...................... 548/531; 548/518; 548/530; 548/519; 548/537; 548/540; 548/543; 548/550; 548/551; 548/538; 548/542; 544/212; 544/207; 544/209; 544/198

[58] Field of Search .............. 548/518, 530, 519, 531, 548/537, 540, 543, 550, 551, 538, 542; 544/212, 207, 209, 198

[56] References Cited

U.S. PATENT DOCUMENTS

| | | | |
|---|---|---|---|
| 3,577,432 | 5/1971 | Helsley | 260/326.3 |
| 4,160,832 | 7/1979 | Laanio et al. | 544/197 |
| 4,234,484 | 11/1980 | Mitzlaff et al. | 260/239 |
| 4,439,545 | 3/1984 | Aspiti et al. | 521/32 |
| 4,448,908 | 5/1984 | Pauly et al. | 523/201 |
| 4,563,431 | 1/1986 | Pauly et al. | 436/533 |
| 4,568,706 | 2/1986 | Noetzel et al. | 521/149 |
| 4,577,031 | 3/1986 | Iovine et al. | 548/319 |

FOREIGN PATENT DOCUMENTS

| | | |
|---|---|---|
| 1161273 | 1/1964 | Fed. Rep. of Germany . |
| 1142710 | 12/1969 | United Kingdom . |
| 1528838 | 10/1978 | United Kingdom . |

OTHER PUBLICATIONS

Epton et al., Polymer, vol. 15, pp. 564–568 (1974).
Epton et al., Polymer, vol. 16, pp. 314–320 (1975).
Hackh's Chemical Dictionary, pp. 27, 62, 4th Edition (1972).
J. Zabransky et al, "Aldehydes and Acetals Based on Acryl- and Methacrylamides as Potential Monomers", Makromol. Chem., 186, 223–229 (1985).
J. Zabransky et al, "Polymers with Aldehyde and Acetal Groups Based on Acryl- and Methacrylamides", Makromol. Chem. 186, 247–254 (1985).
NaBH$_4$ Reduction of Cyclic Imides, J. C. Hubert et al, Tetrahedron, vol. 31, pp. 1437–1441 (1975).
Synthesis of 4-Acyl-2,3-Dihydro-4H-1,4-Oxazines, Massimo Nicola et al, J. Hetrocyclic Chem., vol. 18 (1981), pp. 825–828.
Synthesis and Properties of the α-Keto Acids, Arthur J. L. Cooper et al, Chem. Rev. (1983) vol. 83, pp. 321–358.
Amidoalkylation at Carbon: Recent Advances—Part 1, Harold E. Zaugg, Synthesis, Feb. 1984, pp. 85–110.
Verfahren zur Herstellung Von ω,ω-Dialkoxycarbons-abureestern und-Amiden-Klaus Warning et al., Tetrahedron Letters No. 18, pp. 1563–1564 (1979).
New Methods for Alkaloid Synthesis: α-Acylamino Radical Cyclizations–David J. Hart et al., J. Amer. Chem. Soc., vol. 104, pp. 1430–1432 (1982).
Amidoalkylation in Organic Synthesis.1. Total Synthesis of Isoretronecanol and Trachelanthamidine–George A. Krause, Tetrahedron Letters, vol. 21, pp. 3841–3844 (1980).

Primary Examiner—John M. Ford
Attorney, Agent, or Firm—Michael Leach; James C. Simmons; E. Eugene Innis

[57] ABSTRACT

A compound represented by the following formula:

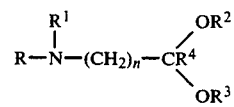

wherein
R is a $C_3$–$C_{24}$ olefinically unsaturated organic radical having functionality which renders the nitrogen atom electron deficient, the olefinic unsaturation functionality being polymerizable,
$R^1$ is hydrogen or a $C_1$–$C_4$ alkyl radical, or
R and $R^1$ together with the nitrogen atom can form an olefinically unsaturated 5 to 7-member ring which has functionality that renders the nitrogen atom electron deficient and the olefinic unsaturation functionality is polymerizable,
$R^2$ and $R^3$ are hydrogen, a $C_1$–$C_4$ alkyl or acyl radical, or
$R^2$ and $R^3$ together are a $C_2$–$C_4$ alkylene group,
$R^4$ is hydrogen or a $C_1$–$C_4$ alkyl, acyl, ester, amide or acid group, and
n is an integer from 1 to 10, provided n is not 1 when R is (meth)acryloyl, $R^2$ and $R^3$ are methyl and $R^1$ and $R^4$ are hydrogen.

Under acidic conditions the above compounds having $R^1$=hydrogen afford cyclic hemiamidals and hemiamide ketals of the following formula

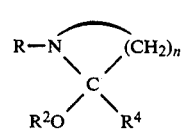

21 Claims, No Drawings

SELF- AND HYDROXYL REACTIVE FORMALDEHYDE-FREE CYCLIC HEMIAMIDAL AND HEMIAMIDE KETAL CROSSLINKING MONOMERS

TECHNICAL FIELD

The present invention relates to olefinically unsaturated monomers which can self-crosslink or react with hydroxy-containing crosslinking agents and can also be incorporated into polymers by free radical addition.

BACKGROUND OF THE INVENTION

Emulsion and solution polymers find wide application as adhesives, binders and coatings. Unfortunately, many of these polymeric materials, especially those prepared predominantly from vinyl acetate, ethylene, vinyl chloride, or their mixtures, show inadequate resistance to water and other solvents in their everyday use. In particular, they experience substantial and unacceptable loss in strength in the presence of solvents such as perchloroethylene, methyl ethyl ketone and toluene. In addition, many of these polymers exhibit deficiencies in adhesion to the substrates on which they are used, for example vinyl acetate, ethylene or vinyl chloride polymers on glass, metal or polyester. These deficiencies are reduced, especially for relatively hydrophilic monomers, by the use of adhesion promoting or crosslinking comonomers and/or post-added crosslinkers.

By far the most successful crosslinking materials are aminoplasts, especially N-methylolacrylamide and urea-formaldehyde condensates. These materials have met substantial success because they are low in cost, highly compatible with aqueous emulsion systems, rapidly cured under acid catalysis, and substrate reactive in that, for example, they react with the hydroxyl groups of cellulose materials. These crosslinking materials, however, suffer from two deficiencies: (1) the emission of low levels of formaldehyde during cure and subsequent use, and (2) inadequate adhesion to certain substrates, for example, metal, glass and polyester.

Many attempts have been made to overcome or minimize the first deficiency, especially after the potential carcinogenicity and irritant properties of formaldehyde became widely recognized.

To reduce the level of formaldehyde in emulsion products, the use of O-alkylated N-methylolacrylamides such as butoxymethylacrylamide or the use of about equimolar ratios of N-methylolacrylamide with acrylamide were introduced. These materials did not, however, totally eliminate the presence of formaldehyde.

Acrylamide/glyoxylic acid condensates and their ethers and esters have been used. These materials have not performed well in applications with vinyl acetate-ethylene emulsions, especially on nonwoven cellulosic substrates. The use of amide/glutaraldehyde condensates, for example the condensate with acrylamide, has also been attempted. The combination of the reagents, however, gave a complex mixture of uncharacterizable products which did not perform well in textile crosslinking applications.

Epoxide functional comonomers such as allyl glycidyl ether, glycidyl (meth)acrylate or their precursors have also been used. These compounds suffered from high costs, limited shelf stability of the functionalized emulsion polymer and toxicity questions associated with epoxide materials.

Other approaches have used esterification chemistry (carboxylic acid plus alcohol to give an ester crosslink), but such approaches require a slow and expensive high temperature curing cycle. Post-addition of formaldehyde-free urea/glyoxal condensates including N,N'-dialkyl-4,5-dihydroxyimidazoles has been used in Japan for fabric treating but such systems are less efficient than formaldehyde-containing analogs.

Thus there is a need for functional monomers which, after incorporation into polymers or copolymers, can be crosslinked under mild conditions with themselves and-/or other polymer or substrate reactive groups to give binders, adhesives and/or coatings with high water and solvent resistance and good substrate adhesion. Such products should also be formaldehyde-free.

SUMMARY OF THE INVENTION

There are provided N-olefinically substituted cyclic hemiamidals and hemiamide ketals, and N-olefinically substituted dialkyl acetals and ketals which can be incorporated into free radical addition polymers. The resulting polymerized monomers undergo efficient acid catalyzed, thermally activated post-crosslinking with themselves or they can react with active hydrogen-containing comonomers of the polymers and/or with groups on the substrate to which the polymer is applied.

The dialkyl acetal and ketal monomers of the invention can be represented by the following general formula I:

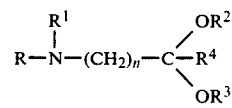

wherein

R is a $C_3$–$C_{24}$ olefinically unsaturated organic radical having functionality which renders the nitrogen atom electron deficient, the olefinic unsaturation being polymerizable, $R^1$ is hydrogen or a $C_1$–$C_4$ alkyl radical, or R and $R^1$ together with the nitrogen atom can form an olefinically unsaturated 5–7 member heterocyclic ring which has functionality that renders the nitrogen atom electron deficient, $R^2$ and $R^3$ are hydrogen, a $C_1$–$C_4$ alkyl or acyl radical, or $R^2$ and $R^3$ together are a $C_2$–$C_4$ alkylene group, $R^4$ is hydrogen or a $C_1$–$C_4$ alkyl, acyl, ester, amide or acid group, and n is an integer from 1 to 10, provided n is not 1 when R is (meth)acryloyl, $R^2$ and $R^3$ are methyl and $R^1$ and $R^4$ are hydrogen.

Under acidic conditions those monomers in which $R^1$ is hydrogen and $R^2$ and $R^3$ do not compose an alkylene group afford N-olefinically substituted cyclic hemiamidals and hemiamide ketals of the following general formula II:

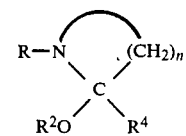

wherein R and R⁴ are as defined above, R² is hydrogen or a C₁–C₄ alkyl or acyl group, and n is 2 to 5, provided R is not an olefinically unsaturated amino carbonyl group when n is 2.

Whenever reference is made to dialkyl acetals and cyclic hemiamidals, it is understood that dialkyl ketals and cyclic hemiamide ketals, respectively, are included.

The N-olefinically substituted cyclic hemiamidals and hemiamide ketals, and the dialkyl acetal and ketal monomers shown especially rapid reactivity and efficient crosslinking with diols such as polyvinyl alcohol. The resulting crosslinked products show excellent solvent and water resistance, low energy cure and good adhesion for application as coatings, binders or adhesives. Foremost they contain no formaldehyde.

The two classes of compounds of the invention equilibrate under acid catalysis with open chain aldehydes and ketones and cyclic iminium ions. The species react: (1) as normal aminoplasts with a second equivalent of hemiamidal, i.e. self-crosslinking; (2) with active hydrogen compounds such as alcohols, amides, acids or amimes; or (3) as aldehydes and ketones with diols, especially 1,2- and 1,3-diols, to give stable acetals and ketals. Covalent attachment of the aldehyde to the nitrogen atom of the molecule prevent loss of aldehyde, for example formaldehyde emissions, and makes possible crosslinking by acetal formation.

The dialkyl acetal and ketal monomers and the cyclic hemiamidal and hemiamide ketal monomers can be free radical polymerized to form homopolymers or copolymers with each other and/or other copolymerizable olefinically unsaturated monomers.

DETAILED DESCRIPTION OF THE INVENTION

The dialkyl acetal and ketal monomers of the invention have the following general formula I:

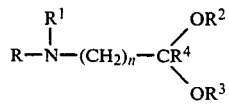

wherein
R is an olefinically unsaturated organic radical having 3 to 24 carbon atoms and functionality which renders the nitrogen atom electron deficient, the olefinic unsaturation being free radical polymerizable.

R¹ is H or a C₁–C₄ alkyl radical, or

R and R¹ together with the nitrogen atom form a heterocyclic olefinically unsaturated organic radical of 5 to 7 atoms composing the ring and having functionality which renders the nitrogen atom electron deficient, R² and R³ are independently hydrogen, a C₁–C₄ alkyl or acyl radical, or R² and R³ together to form a C₂–C₄ alkylene radical, R⁴ is a C₁–C₄ alkyl, acyl, ester, amide or acid radical, but is preferably hydrogen or alkyl, especially hydrogen, and n is a number from 1 to 10, with the proviso that n is not 1 when R is (meth)acryloyl, R² and R³ are methyl and R¹ and R⁴ are hydrogen.

The olefinic unsaturation of the organic radical R should be capable of forming polymers or oligomers with itself or appropriately chosen comonomers under free radical initiation conditions.

Nonlimiting examples of the organic radical R having functionality which renders the nitrogen atom electron deficient are elaborated below. Such radical is capable withdrawing electron density from the nitrogen atom.

Preferably R is an olefinically unsaturated acyl radical represented by the formula

where R⁵ is a C₂ to C₂₃ organic radical having a polymerizable olefinically unsaturated functionality.

Illustrative of olefinically unsaturated organic radicals R are those having the formula: R⁵—C(O)—, and more specifically the following formula:

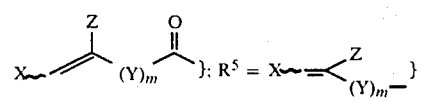

wherein
X is hydrogen or a C₁–C₁₀ alkyl, carboxylic acid, ester, amide group or a nitrile,
Y is —O—, —CH₂O—, —NR⁶—, —CH₂NR⁶—, —(CO)—O—(CH₂)ₐ—NR⁶—, where R⁶ is hydrogen or a C₁–C₄ alkyl radical and a is 1 to 4, —O(-CO)—, —N(CO)—, a branched or unbranched C₁ to C₈ alkylene group, preferably polymethylene, or a substituted or unsubstituted arylene group, especially phenylene,
Z is hydrogen, a C₁–C₄ alkyl, ester, amide or carboxylic acid, or a halogen or nitrile group, and
m is 0 or 1.

R can also represent a vinyl sulfonyl group.

Another example of olefinically unsaturated organic radical R which contains functionality that renders the nitrogen atom electron deficient is vinyl substituted melamine having the following formula:

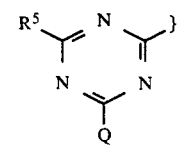

wherein R⁵ is as defined above and Q represents hydrogen, hydroxy, C₁–C₄ alkoxy or alkylamino or

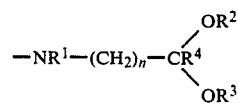

Preferably, R represents a C₃–C₂₄ alkenoyl radical such oleoyl, linoleoyl, and linolenoyl, particularly an alpha, beta-unsaturated C₃–C₁₀ alkenoyl group such as acryloyl, methacryloyl, crotonyl, isocrotonoyl, cinnamoyl, and the like, especially an acryloyl.

Thus the olefinic unsaturated can be incorporated into the monomer by organic radicals

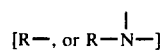

of (meth)acrylamide; maleamides, including maleamic acid, maleamic acid ester, maleamide, fumarate; fumaramic acid; fumaramide; allyl or vinyl carbamate, urea, oxamide or oxamide-ester; vinyl benzamide, vinyl or allyl ether.

$R^1$ is preferably hydrogen but can be a $C_1$-$C_4$ alkyl radical such as methyl, ethyl or butyl. The hydrogen radical is preferred since it permits acid catalyzed intracyclization which n is 2 to 5, preferably 3 or 4, especially n=3, forming the respective cyclic hemiamidals.

In general formula I, R and $R^1$ together with the nitrogen atom can be a 3–6 carbon containing $\alpha,\beta$-unsaturated or alpha-methylene substituted lactam.

$R^2$ and $R^3$ represent hydrogen, $C_1$-$C_4$ alkyl groups, such as methyl, ethyl, isopropyl and butyl, $C_1$-$C_4$ acyl groups such as acetyl and propionyl, or $R^2$ and $R^3$ together may represent a $C_2$-$C_4$ alkylene group such as ethylene, propylene, or butylene. The alkyl groups are preferred, especially methyl and ethyl.

The —$(CH_2)_n$- group linking the nitrogen and the acetal or ketal functionality may also contain heteroatoms such as oxygen and nitrogen, for example, —$CH_2OCH_2$—, or other substituents on the carbon chain, for example, alkyl or aryl substituents.

Since the acetal and ketal compounds are preferred, $R^4$ is preferably hydrogen or a $C_1$-$C_4$ alkyl group such as methyl, ethyl or butyl. The monomer compounds of choice are the dialkyl acetals with $R^4$ being hydrogen.

The monomer compounds of the invention can be prepared by the well-known addition raction of amines to acid chlorides in the presence of a base to remove HCl according to the following general reaction:

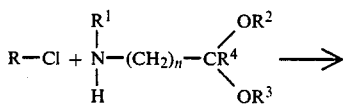

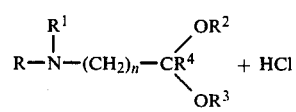

where R, $R^1$, $R^2$, $R^3$, $R^4$ and n are as defined above. For example, a 2-phase reaction involving methylene chloride and aqueous sodium hydroxide can be used. Merely illustrative of numerous acid chlorides which can be used for attaching the respective R group to the respective nitrogen atom are the following:

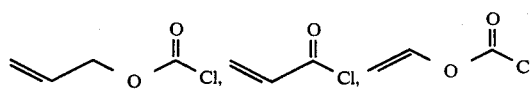

which are readily available materials or can be easily synthesized by well known preparative procedures.

Another reaction for the preparation of the monomer compounds is the addition of aminoacetal compounds to maleic anhydride in an inert solvent as illustrated by the following:

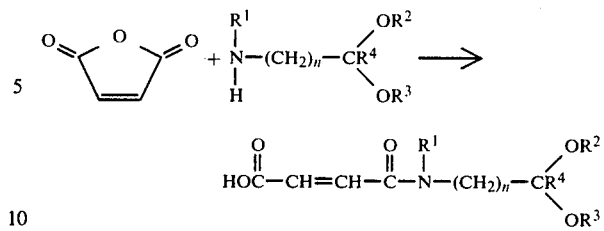

Still another route to the acetal and ketal monomers of the invention comprises reaction of an appropriate olefinically unsaturated carboxylic acid with an amino acetal or ketal using dehydrating agents such as $SOCl_2$ or carbodiimides. The direct reaction of acid and amine is also known, but requires substantially higher temperatures.

In the reaction of an alkylamine with alkyl acrylates to give acrylamides, the frequently observed faster Michael addition of the amine to the double bound produces both Michael addition and amide formation, but at higher temperatures the former reaction is reversible, allowing net formation of N-alkylacrylamides. The Michael reaction can also be suppressed by pre-forming reversible alcohol- or alkylamine-acrylate adducts.

The transamination of olefinically unsaturated amides with the appropriate amino acetal or ketal salt at elevated temperature is another suggested preparative route. The synthesis of acrylamides directly from primary and secondary amines, acetylene and carbon monoxide is known and may prove useful here. The preparation of acrylamides by the Pd catalyzed amidation of vinyl halides with amines and carbon monoxide is also known.

The amino acetals or ketals can be prepared readily by standard organic chemistry synthetic procedures. For example:

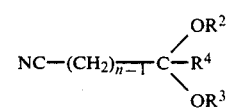

which is readily available from hydroformylation or acrylonitrile in alcohol can be hydrogenated to afford

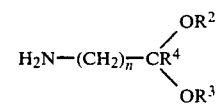

Alternatively, acrolein or methyl vinyl ketone can be treated with HCl in alcohol and then with sodium cyanide and the product hydrogenated.

The dialkyl acetal or ketal monomer of general formula I in which $R^1$ is hydrogen can be cyclized by an acid catalyzed reaction to a hemiamidal or a hemiamide ketal of the invention represented by the general formula II.

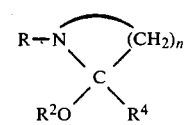

II wherein R and R⁴ are as defined above, R² is hydrogen or C₁–C₄ alkyl or acyl group, and n is 2 to 5, preferably 3 or 4.

The reaction medium may be any typical organic solvent including ketones such as acetone and methyl ethyl ketone, alcohols, methylene chloride and tetrahydrofuran. The reaction medium may contain water in amounts from 0 to 100%. Suitable acid catalysts for performing the cyclization reaction include oxalic acid, p-toluenesulfonic acid, strong acid ion-exchange resins and mineral acids, e.g. HCl and H₂SO₄.

Representative of the dialkyl acetal or ketal monomeric compounds of the invention are the following:
acrylamidobutyraldehyde diethyl acetal (ABDA)
acrylamidobutyraldehyde dimethyl acetal (ABDA-Me)
acrylamidobutyraldehyde dipropyl acetal
acrylamidobutyraldehyde diisopropyl acetal
acrylamidobutyraldehyde dibutyl acetal
acrylamidobutyraldehyde methylethyl acetal
acrylamidobutyraldehyde diacetyl acetal
acrylamidopentanal diethyl acetal (APDA)
acrylamidopentanal dimethyl acetal
acrylamidopentanal dipropyl or diisopropyl acetal
acrylamidohexanal dimethyl acetal
acrylamidohexanal diethyl acetal
acrylamidohexanal dipropyl acetal
acrylamidoheptanal dimethyl acetal
acrylamidoheptanal diethyl acetal
acrylamidoheptanal dipropyl acetal
crotonamidobutyraldehyde dimethyl acetal
crontonamidobutyraldehyde diethyl acetal (CBDA)
crotonamidobutyraldehyde diisopropyl acetal
methacrylamidobutyraldehyde diethyl acetal
methacrylamidobutyraldehyde dimethyl acetal
methacrylamidobutyraldehyde diisopropyl acetal
(meth)acrylamidopropionaldehyde dimethyl acetal
(meth)acrylamidopropionaldehyde diethyl acetal
diethoxybutylmaleamic acid (DBMA)
diethoxybutylmaleamic acid methyl, ethyl or isopropyl ester
cinnamamidobutyraldehyde diethyl acetal (DEBC)
O-allyl-N-(diethoxybutyl)carbamate (ADBC)
O-allyl-N-(dimethoxypentyl)carbamate
O-vinyl-N-(diethoxybutyl)carbamate (DBVC)
O-vinyl-N-(dimethoxypentyl)carbamate
N-vinyl-N'-(dialkoxyethyl)urea or thiourea
N-vinyl-N'-(dialkoxybutyl)urea or thiourea
N-allyl-N'-(dialkoxyethyl)urea (ADEEU) or thiourea
N-allyl-N'-dialkoxybutylurea or thiourea
N-(diethoxybutyl)-N'-(meth)acryloxyethyl urea (DEBMU)
N-(dialkoxypropyl)-N'-(meth)acryloxyethyl urea
N-(diethoxyethyl)-N'-(meth)acryloxyethyl urea (DEEMU) or thiourea
N-allyl-O-dialkoxyethyl carbamate
N-vinyl-O-dialkoxyethylcarbamate
N-(diethoxybutyl)vinylsulfonamide
N-(diethoxybutyl)vinylphosphoramide
N-(diethoxybutyl)vinylbenzenesulfonamide
N-(diethoxybutyl)vinylaniline
N-(diethoxybutyl)vinylbenzylamine
O-(2,2-dialkoxy)propyl-N-(meth)acryloxyethylcarbamate
1-(meth)acrylamidohexan-5-one dialkyl ketal
1-(meth)acrylamido-4,4-dimethylhexan-5-one dialkyl ketal
2,2-dimethyl-5-(meth)acrylamidopentanal dialkyl acetal Illustrative of the cyclic hemiamidals which can be prepared from the above precursors in which a hydrogen atom is attached to the nitrogen atom, in other words R¹ in the general formula I represents hydrogen, are the following compounds:
N-acryloyl-2-ethoxypyrrolidine (AEP)
N-acryloyl-2-methoxypyrrolidine (AMP)
N-(meth)acryloyl-2-hydroxypyrrolidine (AHP)
2-N-(meth)acryloylpyrrolidine acetate
N-(meth)acryloyl-2-alkoxypiperidine
N-(meth)acryloyl-2-hydroxypiperidine
N-(meth)acryloyl-3-alkoxymorpholine
N-(allyloxycarbonyl)-2-alkoxypiperidine
N-(allyloxycarbonyl)-2-alkoxypyrrolidine
N-vinyloxycarbonyl-2-alkoxypyrrolidine
N-vinyloxycarbonyl-2-alkoxypiperidine
1-allyl-5-alkoxy-2-imidazolidone
1-allyl-5-alkoxy-2-imidazolidinethione
1-(meth)acryloxyethyl-5-alkoxy-2-imidazolidone
N[N'-(meth)acryloxyethyl]aminocarbonyl-2-alkoxypyrrolidone
1-allyl-6-ethoxy-(4-methyl)hexahydropyrimidin-2-one (AEMHP)
N-(meth)acryloyl-2-alkoxyperhydroazepine
N-(meth)acryloyl-2-alkoxyazetidine
N-crotonyl-2-alkoxypyrrolidine
N-cinnamoyl-2-alkoxypyrrolidine
N-vinylsulfono-2-alkoxypyrrolidine
N-allylsulfono-2-alkoxypyrrolidine
N-vinylphosphono-2-alkoxypyrrolidine
alkyl N-(but-2-en-1-on-3-carboxylate-1-yl)-2-alkoxypyrrolidine
N-allyl-4-alkoxyoxazolidine-2-one
N-vinylbenzenesulfono-2-alkoxypyrrolidine
N-(vinylphenyl)-2-alkoxypyrrolidine
N-(vinylbenzyl)-2-alkoxypyrrolidine
N-(meth)acryloxyethyl-5-alkoxy-5-methyl-2-imidazolidone
N-(meth)acryloxyethyl-4-alkoxy-4-methyloxazolidone
N-(meth)acryloyl-2-alkoxy-2-methylpyrrolidine
N-(meth)acryloyl-2-hydroxy-2,3,3-trimethylpiperidine
Alkyl N-allyl-5-alkoxypyrrolidone-5-carbonylate
N-[3-(alkoxycarbonyl)acryloyl]-2-alkoxypyrrolidine The dialkyl acetal and ketal compounds and the cyclic hemiamidal and hemiamide ketal compounds of the invention being olefinically unsaturated can be homopolymerized, or polymerized in any amount, for example, ranging from greater than 0 to over 99 wt% with each other and/or other copolymerizable monomers. It is preferred that the copolymers contain about 0.5 to 10 wt% of the acetal, ketal and/or cyclic hemiamidal or hemiamide ketal monomers of the invention, especially about 1 to 3 wt% in nonwoven binder polymers.

Suitable copolymerization monomers include monoolefinically and polyolefinically unsaturated monomers including C₃–C₁₀ alkenoic acids, such as acrylic, methacrylic, crotonic and isocrontonic acids and their esters with C₁–C₁₈ alkanols, such as methanol, ethanol, propanol, butanol and 2-ethylhexyl alcohol; alpha, beta-unsaturated C₄–C₁₀ alkenedioic acids such as maleic acid, fumaric acid and itaconic acid and their monoesters and diesters with the same C₁–C₁₈ alkanols; vinyl halides such as vinyl chloride and vinyl fluoride; vinylidene halides such as vinylidene chloride; alkenes, such as ethylene, propylene and butadiene; styrene, vinyltoluene and other substituted styrenes; and nitrogen containing monoolefinically unsaturated monomers, particularly nitriles, amides, N-methylol amides, lower alkanoic acid esters of N-methylol amides, lower alkyl ethers of N-methylol amides and allyl carbamates, such as acrylonitrile, acrylamide, methacrylamide, N-methylolacrylamide, N-methylol methacrylamide, N-methylol allyl carbamate and N-methylol lower alkyl ethers and N-methylol lower alkanoic acid esters of N-methylolacrylamide, N-methylol methacrylamide and N-methylol allyl carbamate; vinyl esters of $C_1$–$C_{18}$ alkanoic acids, such as vinyl formate, vinyl propionate, vinyl laurate and especially vinyl acetate; vinyl ethers, such as methyl vinyl ether and isobutyl vinyl eter; and vinylamides such as N-vinyl pyrrolidone, N-vinylacetamide and N-vinylformamide.

The cyclic hemiamidal and hemiamide ketal monomers and the dialkyl acetal and ketal monomers can be homopolymerized, copolymerized with each other or copolymerized with at least one of the above copolymerizable monomers by solution or aqueous emulsion polymerization techniques well known in the art. Such polymerization techniques are described in such chemistry texts as *Polymer Synthesis*, Vol. I and II, by S. R. Sandler and W. Karo, Academic Press, New York and London (1974), and *Preparative Methods of Polymer Chemistry*, Second Edition, by W. R. Sorenson and T. W. Campbell, Interscience Publishers (John Wiley and Sons), New York (1968). Solvents which are suitable for solution polymerization include toluene, isopropanol, ethanol, methanol, benzene, acetone, ethyl acetate, acetonitrile, dimethylformamide, methyl ethyl ketone and water.

The monomers in the polymerization recipe can be added all at once or metered into the polymerization reaction medium incrementally in an intermittent or continuous, preferably uniform, addition rate or any combination thereof in order to take advantage of the various polymerization reactivities of the various monomers.

Catalytically effective amounts of various free-radical forming materials can be used in carrying out the polymerization of the monomers, such as peroxide compounds like peracetic acid, benzoyl peroxide, and persulfate salt and azo compounds. Combination-type systems employing both reducing agents and oxidizing agents can also be used, i.e. a redox system. Suitable reducing agents, or activators include bisulfites, sulfoxylates, or other compounds having reducing properties such as ascorbic acid, erythrobic acid and other reducing sugars. The oxidizing agents include hydrogen peroxide, organic peroxides such as t-butyl hydroperoxide and the like, persulfates, such as ammonium or potassium persulfate, and the like. Specific redox systems which can be used include hydrogen peroxide and zinc formaldehyde sulfoxylate; t-butylhydroperoxide and erythorbic acid; hydrogen peroxide, ammonium persulfate, potassium persulfate or t-butyl hydroperoxide with sodium metabisulfite, sodium bisulfite, ferrous sulfate, zinc formaldehyde sulfoxylate, sodium formaldehyde sulfoxylate or sodium acetone bisulfite. Other free radical forming systems that are well known in the art can also be used to polymerize the monomers.

The oxidizing agent is generally employed in an amount of 0.01 to 1%, preferably 0.05 to 0.5% based on the weight of the monomers introduced into the polymerization system. The reducing agent is ordinarily added dissolved in an appropriate solvent in the necessary equivalent amount.

With regard to aqueous emulsion polymerization techniques, again any of the well known emulsifying agents can be used, such emulsifying agents include ionic and nonionic surfactants such as sodium lauryl sulfate, sodium sulfosuccinate esters and amides, sulfonated alkyl benzenes, alkylphenoxy polyethoxy ethanols and other polyoxyethylene condensates.

The concentration range of the total amount of emulsifying agents useful is from less than 0.5 to 5% based on the aqueous phase of the emulsion regardless of a solids content.

Where necessary to maintain the pH of the aqueous emulsion reaction medium, typical buffering systems can be employed.

In addition to or in place of the surfactants, protective colloids such as polyvinyl alcohol and celluloses like hydroxyethyl cellulose, methyl cellulose, hydroxypropyl methyl cellulose and the like can be used as the emulsifying, or stabilizing, agent.

The cyclic hemiamidals and dialkyl acetal and ketal monomers of the invention are a more general case of which normal amide/aldehyde adducts are a specialized example. Regarding the prior art technology, the product copolymers of N-methylolacrylamide (NMA), which is a condensate of acrylamide and formaldehyde, (1) crosslink efficiently under acid catalysis via methylol or methylene coupling, (2) react well with substrates containing active hydrogen, e.g. cellulose and (3) are low in cost. However, the formaldehyde is only weakly bound to the amide group of NMA and both the initial and cured product can give off low but measurable levels of formaldehyde, a suspect as a cancer-causing agent. Substitution of other aldehydes or ketones usually exacerbates this problem, as their equilibria shift towards starting materials even more than formaldehyde containing systems do.

The compounds of this invention circumvent this problem by attaching the aldehyde or ketone to the nitrogen (amide) portion of the molecule via a covalent chain. Especially when this chain is of an appropriate length to give a 5 or 6-membered ring with the nitrogen atom, the equilibria strongly favor the cyclized material. With or without a favorable equilibrium, the aldehyde cannot be lost to the solution or the atmosphere. A practical example of this concept is shown.

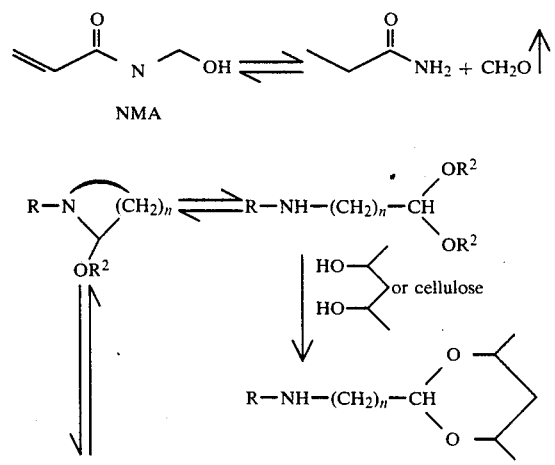

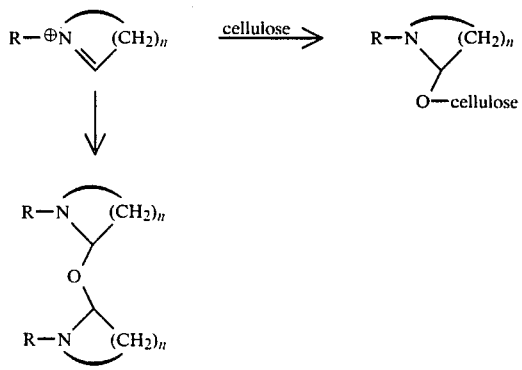

Here the aldehyde is protected as its dialkyl acetal. As demonstrated by the data and some model experiments described in the experimental section, these compounds interconvert under acid catalysis and can usually be used interchangeably in polymer and other applications.

To a first approximation, the cyclized form undergoes the same self-crosslinking and coupling with active hydrogen containing compounds as observed with NMA. Unlike NMA and other aldehyde based aminoplasts, both the dialkyl blocked aldehyde and ketone monomers and the cyclic hemiamidal and hemiamide-ketal forms also contain a covalently bound blocked aldehyde or ketone which can react effectively with 1,2- and 1,3-diols, such as ethylene glycol, 1,2- and 1,3-propylene glycol, 1,2- and 1,3- butylene glycol, 2,4-pentanediol and the like; a feature particularly useful in reactions with polyvinyl alcohol which is 30 to 100% hydrolyzed or cellulose and cellulose derivatives such as methyl cellulose, hydroxyethyl cellulose, hydroxypropyl cellulose and the like; or for adhesion to metal oxide and other surfaces. Obviously, no formaldehyde is involved in the synthesis or decomposition of these compounds.

The reaction of the dialkyl acetal/ketal monomers and the cyclic hemiamidal/hemiamide ketal monomers with active hydrogen-containing compounds and substrates, such as the 1,2- and 1,3-diols, polyvinyl alcohol, cellulose and metal oxide surfaces, can be catalyzed using acidic materials such as mineral acids, like hydrogen chloride, or organic acids, like oxalic acid or acid salts such as ammonium chloride as is well known in the art of acetal and ketal formation and reaction.

The efficacy of these compounds in achieving lower energy cure than standard aminoplasts is not completely understood at this time. The reactivity of these materials may simply be due to the fact that the intermediate N-acyliminium ion in the rection from cyclohemiamidal to crosslinked or substrate bound product is stabilized relative to the unsubstituted acyliminium species formed with formaldehyde based aminoplasts. In the presence of 1,2- or 1,3-diols the thermodynamically favored formation of cyclic acetals may provide a cure accelerating mechanism.

Most previous attempts to solve this problem of formaldehyde liberation have not used aminoplasts in which the aldehyde is bound via a covalent linkage to the nitrogen atom, for example amide portion of the aminoplast molecule. This difference existing in the monomers of the invention produces a number of beneficial results:

(a) the aldehyde cannot diffuse away from the amide portion of the molecule to produce toxic or irritating emissions, free radical inhibition, or discoloration, as observed even with the electron deficient aldehydes or formaldehyde used in prior art technology.

(b) the presence of bound and blocked aldehyde functionality allows efficacious reaction with 1,2- and 1,3-diols to give particularly thermodynamically stable acetal formation, an additional crosslinking mode not available to prior art systems; and (c) use of a substituted hemiamidal often produces faster reaction then observed with other species.

Contemplated as the functional equivalent of 1,2- and 1,3-diols for the purpose of this invention are 1,2- and 1,3-amine alcohols and diamines.

In addition, the ability to prepare enamides through loss of $HOR^2$ from cyclic hemiamidals may prove important in crosslinking applications.

The dialkyl acetal/ketal and cyclic hemiamidal/hemiamide ketal monomers of the invention and their derived polymers are suitable for use as crosslinkers and adhesion promoting agents in paints and other coatings, adhesives for glass, wood, paper, metal, ceramics and other substrates; formaldehyde free binders for nonwoven products, medical/surgical applications, diaper cover stock, wipes, towels, apparel, carpeting, fabrics, filtration products and home furnishings. They may also be useful as co-reagents to reduce formaldehyde and/or improve adhesion and other performance factors when used with standard aminoplasts and phenoplasts.

The polymers derived from the dialkyl acetal/ketal monomers and cyclic hemiamidal/hemiamide ketal monomers of the invention are useful as binder compositions in the preparation of nonwoven products, or fabrics, by a variety of methods known to the art which, in general, involve the impregnation of a loosely assembled mass of fibers with the copolymer binder emulsion, followed by moderate heating to dry the mass. This moderate heating also usually serves to cure the binder by forming a crosslinked interpolymer. Before the binder is applied it is, of course, mixed with a suitable catalyst for the crosslinking monomer. For example, an acid catalyst such as mineral acids, e.g. hydrogen chloride, or organic acids, e.g. p-toluenesulfonic acid, or acid salts such as ammonium chloride, are suitably used as is known in the art. The amount of catalyst is generally about 0.5 to 2% of the total resin. It has been discovered with respect to the binder polymers prepared using the monomers of the invention that simple amine acid salts, such as ammonium chloride, ammonium acetate and methyl ammonium chloride are surprisingly the preferred catalysts for crosslinking.

The starting fiber layer or mass can be formed by any one of the conventional techniques for depositing or arranging fibers in a web or layer. These techniques include carding, garnetting, air-laying and the like. Individual webs or thin layers formed by one or more of these techniques can also be laminated to provide a thicker layer for conversion into a fabric. Typically, the fibers extend in a plurality of diverse directions in general alignment with the major plane of the fabric, overlapping, intersecting and supporting one another to form an open, porous structure.

When reference is made to "cellulose" fibers, those fibers containing predominantly $C_6H_{10}O_5$ groupings are meant. Thus, examples of the fibers to be used in the starting layer are the natural cellulose fibers such as wood pulp, cotton and hemp and the synthetic cellulose fibers such as rayon, and regenerated cellulose. Often the fiber starting layer contains at least 50% cellulose fibers whether they be natural or synthetic, or a combination thereof. Often the fibers in the starting layer may comprise the natural fibers such as wool, jute; artificial fibers such as cellulose acetate; synthetic fibers such as cellulose acetate, polyvinyl alcohol, polyamides, nylon, polyester, acrylics, polyolefins, i.e. polyethylene, polyvinyl chloride, polyurethane, and the like, alone or in combination with one another.

The fiber starting layer is subjected to at least one of the several types of bonding operations to anchor the individual fibers together to form a self-sustaining web. Some of the better known methods of bonding are overall impregnation, or printing the web with intermittent or continuous straight or wavy lines or areas of binder extending generally transversely or diagonally across the web and additionally, if desired, along the web.

The amount of binder, calculated on a dry basis, applied to the fibrous starting web is that amount is at least sufficient to bind the fibers together to form a self-sustaining web and suitably ranges from about 3 to about 100% or more by weight of the starting web, preferably from about 10 to about 50 wt% of the starting web. The impregnated web is then dried and cured. Thus the fabric is suitably dried by passing it through an air oven or the like and then through a curing oven. Typical laboratory conditions to achieve optimal crosslinking are sufficient time and temperature such as drying at 150°-200° F. (66°-93° C.) for 4 to 6 minutes, followed by curing at 300°-310° F. (149°-154° C.) for 3 to 5 minutes or more. However, other time-temperature relationships can be employed as is well known in the art, shorter times at higher temperatures or longer times at lower temperatures being used.

The monomers of the invention may also be useful as reactive diluents in coating compositions in which the aldehyde/cyclic hemiamidal moiety reacts first and the double bonds are reacted later by free radical or nucleophilic attack.

In addition, the compounds may be useful for modifying or functionalizing polyvinyl alcohol, cellulosics (wood, paper, rayon, cotton), starch or sugars through formation of cylic acetals with 1,2- or 1,3-diols.

The following examples are illustrative of the invention and are not intended to limit the scope thereof.

EXAMPLE 1

Synthesis of Acrylamidobutyraldehyde Diethyl Acetal (ABDA)

4-Aminobutyraldehyde diethyl acetal (AmBDA, 75 g, 1.09 mol, Aldrich Chemical) was combined with a two phase mixture of 955 mL of $CH_2Cl_2$ and 160 mL of 14N NaOH in a 3 neck flask equipped with a thermometer and an efficient mechanical stirrer. This was cooled to 15° C. with an ice bath. Acryloyl chloride (98.3 g, 1.09 mol, Aldrich) was added via an addition funnel at a rate slow enough to maintain the reaction temperature below 30° C. Reaction monitoring by capillary glpc revealed essentially complete AmBDA consumption when the acryloyl chloride addition was complete. Agitation was continued for 1 h. The layers were separated (water may be added to dissolve precipitated salt and improve phase separation) and the organic phase was washed with saturated brine. The brine was combined with the aqueous layer and back extracted with $CH_2Cl_2$. The combined organic layers were neutralized with saturated aqueous $NaH_2PO_4$, dried over anhydrous $MgCl_2$ and concentrated on a rotary evaporator at 40° C. to give 99% pure ABDA (by glpc) in 87% yield. The product can be freed of any high molecular weight by-products by kugelrohr distillation (120°–125° C. at 0.2 torr), but this produces significant yield losses and partial isomerization to N-acryloyl-5-ethoxy pyrrolidine (AEP) and related products. The pot temperature should not exceed 60° C. during these operations. The yield loses are minimized by adding a basic reagent, such as $Na_2CO_3$, and a radical inhibitor, such as methylene blue, to the distillation vessel.

IR(film): 3260, 1655, 1630, 1540 $cm^{-1}$.

$^1$H NMR ($CDCl_3$): δ6.25 (dd, 1, J=16.8, J=2.0 Hz, vinyl), 6.13 (v br, 1, NH), 6.10 (dd, 1, J=16.8, J=9.6 Hz, vinyl), 5.60 (dd, 1, J=9.6, J=2.0 Hz, vinyl), 4.48 (br t, 1, J~4.6 Hz, CH), 3.75–3.4 (m, 4, $OCH_2$), 3.32 (br q, 2, J~6.1 Hz, $NCH_2$), 1.65 (m, 4, $CH_2CH_2$), and 1.20 (t, 6, J=6.9 Hz, $CH_3$). The vinyl region changes on dilution or in other solvents. $^{13}$C NMR: δ125.65 (t), 131.38 (d), 165.93 (s), 39.36 (t), 24.65 (t), 31.32 (t), 102.78 (d), 61.43 (t, 2C), 15.37 (t, 2C). MS: m/e 47, 55, 70, 75, 103, 123, 124, 169, 170, 186, 214 (CI: $M^+=215$)

Anal. Calc'd for $C_{11}H_{22}NO_3$: C, 61.37; H, 9.83; N, 6.51. Found: C, 61.24; H, 9.87; N, 6.44.

EXAMPLE 2

Direct Synthesis of N-acryloyl-5-ethoxy pyrrolidine (AEP)

AmBDA (125 g, 0.78 mol) was mixed as above with 835 mL of $CH_2Cl_2$ and 124 mL of 14N NaOH. After cooling the mixture to 18° C., acryloyl chloride (70 g, 0.78 mol) was added with efficient stirring to maintain the reaction temperature below 30° C. (approximately one h). Shortly after acid chloride addition was completed, the AmBDA was observed by glpc to be consumed, producing 97% pure ABDA. Without an additional reaction period, the combined layers were neutralized to pH 7.4 with concentrated $H_2SO_4$ and separated. The organic layer was dried with $MgSO_4$ and an aliquot was extracted with $H_2O$ to give a pH of 4.2, indicating hydrolysis or reaction of a low residual level of acryloyl chloride to generate HCl. The organic layer was again neutralized (to pH 7.2) with alcoholic KOH and concentrated on a rotary evaporator to yield 108 g of light yellow liquid, 89% AEP (83.4% yield) and 2% ABDA. MEHQ (1000 ppm) was added as an inhibitor.

EXAMPLE 3

Synthesis of AEP from ABDA

A 40 g sample of ABDA analyzing as 70.1% ABDA and 23.9% AEP was mixed with 400 mL of 3:1 $CH_2Cl_2$/EtOH and 10 g of strong acid macroreticular ion exchange resin (Rohm and Haas XN-1010). The mixture was stirred at room temperature and analyzed hourly by capillary glpc. Peak ratios were 83.2% AEP and 11.1% ABDA after 1 h, and 87.0% AEP, 7.8% ABDA after 2 h and at 3 h. The resin was filtered off and the solvent removed. Kugelrohr distillation after neutralization (pH 6.4 with KOH/EtOH) gave 28.7 g of product (90°–96° C., 0.15 torr) containing 92% AEP (77.5% yield based on ABDA conversion).

IR (film): 1645, 1610, 1445 $cm^{-1}$.

$^1$H NMR ($D_2O$): δ6.45 (8 peak m, overlapping dd's, 1, J=10.4, J=16.8 Hz, vinyl), 6.12 (overlapping dd's, 1, J=16.8, J~1.6 Hz, vinyl), 5.70 (overlapping dd's, 1, J~10, J~1.6 Hz, vinyl), 5.33 (d, ~0.3, J=4.8 Hz, CH)+5.21 (d, ~0.6, J=4 Hz, CH), 3.45 (m, 3, OCH$_2$), 2.19 (m, 1), 2.1-1.4 (m, 4, CH$_2$CH$_2$). 1.03 (overlapping t's, 3, J=6.5 Hz, CH$_3$). M/S: 41, 55, 70, 86, 96, 112, 124, 125, 140 (CI (NH$_3$): M$^+$ =169)

EXAMPLE 4

Synthesis of Acrylamidoacetaldehyde Dimethyl Acetal (AADMA)

To 125 g (1.19 mol) of aminoacetaldehyde dimethyl acetal in a rapidly stirred two phase mixture of 390 mL of methyl t-butyl ether (MTBE) and 125 mL of 14N aqueous NaOH at 18° C. was added 107.5 g (1.19 mol) of acrylol chloride over 1 h (reaction temperature maintained below 30° C.). A precipitate (NaCl) separated out. After 15 min the pH was adjusted to 7.1-7.8 (dil. NaOH) and the layers were separated. The product was extracted into H$_2$O (hexane added to the MTBE to drive the equilibrium). GC analysis showed 181 g AADMA in 700 mL of aqueous solution, plus 10 g AADMA in the brine layer (100% yield).

EXAMPLE 5

Synthesis of AADMA with Product Isolation

Example 44 was repeated with 20 g of aminoacetaldehyde dimethyl acetal (0.19 mol), 17.2 g (0.19 mol) of acryloyl chloride, 125 mL of MTBE and 20 mL of 14N NaOH. The separated organic layer was washed with brine. Additional aqueous extraction of the organic layer produced significant product loss to the aqueous phase. The aqueous layer was back-extracted two times with Et$_2$O. The combined organic layers were dried with anhydrous MgSO$_4$ and concentrated on a rotary evaporator to give 25.5 g of light yellow liquid analyzing as 95% AADMA (84%). Cu bronze, 1000 ppm, was added to this product and the mixture was subjected to kugelrohr distillation (105° C., 0.11 torr) to give 4 g of colorless distillate before the remainder resinified. The distilled product began to resinify after several days in a freezer despite the addition of MEHQ inhibitor (1000 ppm).

IR (film): 3290 (br), 1660, 1624, 1610 (sh), 1545 cm$^{-1}$.

$^1$H NMR (CDCl$_3$): δ6.3 (dd, 1, J=16.5, J=1.9 Hz, vinyl), 6.2 (dd, 1, J=16.5, J=9.6 Hz, vinyl+buried NH), 5.65 (dd, 1, J=9.6, J=1.9 Hz, vinyl), 4.43 (br t, 1, CH), 3.48 (apparent t, 2, NCH$_2$), 3.4 (S, 6, CH$_3$).

EXAMPLE 6

Synthesis of N-(2,2-Dimethoxyethyl)maleamic acid (DMEMA)

Aminoacetaldehyde dimethyl acetal (90 g, 0.857 mol) was added over 45 min to a 16° C. mixture of 84 g (0.857 mol) of purified maleic anhydride (azeotropic removal of H$_2$O by distillation of xylene from crude anhydride) in 855 mL of CH$_2$Cl$_2$ (reaction temperature below 30° C.). After 1 h all of the amine had reacted and the solvent was removed on a rotary evaporator to yield a yellow solid. Recrystallization from MeOH gave 138 g (75% yield) of white solid, mp 91°-92° C. Further recrystallization (toluene/MeOH) gave mp 93°-94.5° C.

IR: 3280, 1710, 1630, 1600, 1540 cm$^{-1}$.

$^1$H NMR (CDCl$_3$): δ7.19 (br s, 1, NH), 6.38 (s, 2, vinyl), 4.49 (t, 1, J=5.0 Hz, CH), 3.55 (2d, 2, J~5 Hz, CH$_2$) 3.41 (s, 6, CH$_3$); (CD$_2$Cl$_2$): δ15.68 (s, 1, CO$_2$H), 6.30, 6.31 (d's, 2, J=12.2 Hz, vinyl), 6.76 (1, NH), 4.49 (t, 1, J=4.9 Hz, CH), 3.56 (2d, 2, J=4.9 Hz), 3.40 (s, 6, CH$_3$).

EXAMPLE 7

Synthesis of O-Allyl-N-(4,4-diethoxybutyl)carbamate (ADBC)

(1) Two phase To 3.22 g (2.0 mmol) of 4-aminobutyraldehyde diethyl acetal in a two phase rapidly stirred mixture of 20 mL of CH$_2$Cl$_2$ and 20 mL of 2N NaOH at 0° C. was added 2.41 g (2.0 mmol) of allyl chloroformate (temperature maintained below 30° C.). The layers were separated and the organic layer was washed with H$_2$O and dried over 3 A molecular sieves. The solution was concentrated on a rotary evaporator to yield a light yellow liquid.

(2) Single phase Ethanol (50 ml) was cooled to 0° C. and treated with 2.41 g of allylchloroformate and 3.22 g of aminobutyraldehyde diethyl acetal. After 20 min the pH was 1.8, after 35 min it was 1.2. The sample was neutralized slowly with triethylamine (22.4 mL to a stable pH of 7.3 (1 hr.)). The mixture was concentrated at 50° C., diluted with CH$_2$Cl$_2$ and reconcentrated. On Et$_2$O dilution, a white precipitate of Et$_3$NHCl (mp 256° C.) separated. The Et$_2$O solution was washed (H$_2$O and brine) and filtered through 3 A molecular sieving zeolite. Concentration yielded 3.42 g of yellow liquid.

IR (film): 3320 (NH), 1700 (carbamate), 1650 (vinyl), 1520 (NH), 1060 cm$^{-1}$; $^1$H NMR (CDCl$_3$): δ5.91 (m, 1, J~5.6 Hz, vinyl), 5.28 (dd, 1, J=16.6, J~1.6, vinyl), 5.20 (dt (?), 1, J=10.3, vinyl), 5.05 (br, 1, NH), 4.58 (br t, 2, J~5 Hz, allyl), 4.49 (t?, 1, J~4.7 Hz, CH), 3.58 (m, 4, OCH$_2$), 3.2 (q, ~2, J~5.6 Hz, NCH$_2$), 1.6$_3$ (m, 4, CH$_2$CH$_2$), 1.2 (t, 6, J=6.8 Hz, CH$_3$).

EXAMPLE 8

O-Allyl Carbamate of 2-Ethoxypyrrolidine by the Isomerization of ADBC

ADBC (2 g) was added to 20 mL of CH$_2$Cl$_2$ and anhydrous HCl was bubbled through the mixture for 5 min. The solution was heated to 38° C. for 1.5 h. The sample was washed with H$_2$O and the aqueous phase was back-extracted with CH$_2$Cl$_2$. The combined organics were dried with MgSO$_4$ and concentrated to yield 1.33 g of yellow liquid. This sample (0.75 g) was submitted to preparative thin layer chromatography on silica gel (3:1 Et$_2$O/hexane) to yield 5 spots by UV: rf 0.58 (30 mg), 0.49 (145 mg), 0.41 (135 mg), 0.26 (129 mg), origin (26 mg). The remainder also gave 107 mg of mixed fractions. The second and third fractions were largely the desired O-allyl carbamate of 2-ethoxypyrrolidine:

IR: no NH, 1700, 1650 (sh), 1400 cm$^{-1}$.

$^1$H NMR (CDCl$_3$): δ5.95 (m, 1, vinyl), 5.4-5.25 (m, 3, vinyl+NCHO), 4.63 (d, 2, allyl), 3.75-3.3 (m, 4, OCH$_2$+NCH$_2$), 2.2-1.65 (m, 4, CH$_2$CH$_2$), 1.2 (t, 3, CH$_3$).

The remaining fractions were largely the O-allyl carbamate of 2-hydroxy pyrrolidine:

IR (film): 3420, 1690, 1650 (sh), 1400 cm$^{-1}$.

$^1$H NMR (CDCl$_3$): δ5.95 (m, 1, vinyl), 5.43 (br d, 1, vinyl), 5.2 (m, ~2, vinyl+NCHO), 4.6 (br d, 2, allyl), 3.7-3.1 (m, 2, NCH$_2$), 2.1-1.5 (m, 4, CH$_2$CH$_2$).

EXAMPLE 9

Synthesis of N-(4,4-Diethoxybutyl)maleamic Acid (DBMA)

Maleic anhydride (85 g) in 1300 mL of $CH_2Cl_2$ was cooled to 15° C. and treated with 155 g of 4-aminobutyraldehyde diethyl acetal (AmBDA). (Other preparations used the reverse mode of addition with similar results.) Fifteen min after the addition was complete no further AmBDA was detected by glpc. The solvent was removed under reduced pressure (maintained at 0.2 torr for 2 h to assure completion) to give 230 g of slightly orange colored thick oil. On standing for several months at 0° C., this material solidified to an off-white solid.

IR (film): 3260 (NH), 1700 (amide), 1630, 1550 $cm^{-1}$.

$^1$H NMR ($CD_2Cl_2$): $\delta \sim 14$ (v br, $\sim 1$, $CO_2H$), 8.83 (br t, 1, NH), 6.43 (d, 1, J=13.3 Hz, vinyl), 6.25 (d, 1, J=13.3 Hz, vinyl), 4.47 (br t, 1, CH), 3.7–3.4 (m, 4, $OCH_2$), 3.34 (m, 2, $NCH_2$), 1.63 (br s, 4, $CH_2CH_2$), 1.20 (t, 6, J=6.8 Hz, $CH_3$).

EXAMPLE 10

Synthesis of 4-Acetamidobutyraldehyde Diethyl Acetal

This reaction followed the procedure of Example 1, but using 50 g (0.31 mol) of AmBDA, 24.3 g (0.31 mol) of acetyl chloride, 330 mL of $CH_2Cl_2$ and 50 mL of 14N NaOH. Thirty min after the acid chloride addition was completed the reaction was adjusted to pH 7.7 with 30% $H_2SO_4$ and solid $CO_2$ was added to give a pH of 6.4. The separated aqueous layer was extracted with $CH_2Cl_2$ and the combined organic layers were washed with brine, dried with anhydrous $MgSO_4$ and concentrated to give 69 g of pale yellow liquid. This sample plus 1000 ppm of MEHQ and 0.6 g of copper bronze were distilled on a kugelrohr apparatus (120° C., 0.02 torr) to give 45 g of colorless oil (65% yield).

IR: (film) 3290, 1650, 1555, 1440 $cm^{-1}$.

$^1$H NMR ($CDCl_3$): $\delta 6.40$ (br s, 1, NH), 4.64 (t, imp. or CH rotamer), 4.47 (t, $\sim 1$, J=5 Hz, CH), 3.4–3.75 (m, 4, $OCH_2$), 3.23 (q, 2, J=6.5 Hz, $NCH_2$), 2.62 (m, 4, $CH_2CH_2$), 1.96 (s, 3, $CH_3$), 1.20 (t, 6, J=7.2 Hz, $CH_3$).

EXAMPLE 11

Synthesis of 4-(Aminoethyl)butyraldehyde Diethyl Acetal

Acetamidobutyraldehyde diethyl acetal (25 g, 0.123 mol) was slowly added to 4.7 g (0.123 mol) of lithium tetrahydridoaluminum in 150 mL of dry THF at reflux. After 1 h the excess $LiAlH_4$ was destroyed by adding EtOAc and the reaction was treated with 1–2 mL of saturated aqueous $Na_2SO_4$. The green gelatinous mixture was vacuum filtered and the organic phase was concentrated on a rotary evaporator. The inorganic phase was extracted with EtOAc and again with THF and the combined concentrated organic phases were distilled on a kugelrohr apparatus (105°–130° C. at 0.2 torr) to yield 9.26 g of yellow liquid. Capillary gc analysis and nmr revealed the mixture to be 75% 4-(aminoethyl)butyraldehyde diethyl acetal (30% yield).

IR: (film) 1745 (v.w., imp) 1655 (w), 1450, 1126, 1063 $cm^{-1}$.

$^1$H NMR ($CDCl_3$): $\delta 5.66$ (t, imp?), 5.51 (Tt$\sim 1$, J=5 Hz, CH), 3.4–3.75 (m, 4, $OCH_2$), 2.7–2.3 (m, $\sim 4$, $CH_2NCH_2$), 1.61 (m, $\sim 4$, $CH_2CH_2$), 1.21 (t, J=3.5 Hz), 1.11 (t, J=3.5 Hz)+1.02 (t, J=3.5 Hz) last three in 62:17:20 ratio, rotamer mix.

EXAMPLE 12

Synthesis of N-Ethylacrylamidobutyraldehyde Diethyl Acetal (Et-ABDA)

4-(Aminoethyl)butyraldehyde diethyl acetal (8.5 g, 0.045 mol) in 56 mL of $CH_2Cl_2$ was rapidly stirred with 8 mL of 14N NaOH at 20° C. Acryloyl chloride (3 g, 0.045 mol) was added slowly to maintain the temperature below 30° C. GC analysis at 30 min showed no remaining starting material and a new product at 8.65 min. The mixture was neutralized with 30% $H_2SO_4$ and buffered with solid $CO_2$. The organic phase was concentrated and distilled (kugelrohr) to give 6.5 g of yellow liquid (100°–125° C., 0.15 torr). GC analysis showed 82% of the 8.65 min peak (53% yield) plus 4 minor components.

$^1$H NMR ($CDCl_3$): $\delta 6.56$ (dd, <1, J=10.3 Hz, J=16.2 Hz, vinyl), 6.32 (dd, <1, J=16.2 Hz, J=2.0 Hz, vinyl), 5.65 (dd, <1, J=10.3 Hz, J=2.0 Hz, vinyl), 4.47 (br t, 1, methine), 3.8–3.2 (m, $\sim 8$, $NCH_2$, $OCH_2$), 1.65 (m, 4, $(CH_2)_2$), 1.20 (t, 9, J=6.7 Hz, $CH_3$).

EXAMPLE 13

Reactions of N-Acetyl-4-aminobutyraldehyde Diethyl Acetal (1) In MeOH. N-Acetyl-4-aminobutyraldehyde diethyl acetal (A) (15 g) was added to 185 mL of 3:1 $CH_2Cl_2$/MeOH. Rohm and Haas XN-1010 strong acid macroreticular ion exchange resin (4 g) was added and the mixture was stirred slowly at ambient temperature. After 15 minute, analysis by glpc showed additional components at shorter retention times than A. At 1.5 h the XN-1010 was filtered off and the solution was concentrated to give 13.8 g of light yellow liquid analyzing as 70% N-acetyl-2-methoxy-pyrrolidine (E, retention time 5.66 min), 6.4% N-acetyl-2-ethoxy-pyrrolidine (D, r.t. 5.99 min), 17.3% N-acetyl-4-aminobutyraldehyde dimethylacetal (C, r.t.=7.05 min), 3% N-acetyl-4-aminobutyraldehyde ethyl methyl acetal (B, r.t.=7.34 min), and 1.6% N-acetyl-2-pyrroline (G, r.t.=4.74 min).

E, $^1$H NMR ($CDCl_3$): $\delta 5.43$ (d, 0.4, J=4.6 Hz, NCHO)+4.96 (d, 0.6, J=4 Hz, NCHO), 3.48+3.39 (s's, 3, $CH_3$), 3.8-3.3 (m, $NCH_2+OCH_2CH_3$ imp?), 3.30 (s, MeOH?), 2.16+2.09 (s's, 3, $\bar{C}H_3$), 2.2-1.6 (m, 4, $CH_2CH_2$). This sample contains signals attributable to the ethyl acetal and ethanol by glpc. GC/MS: m/e 43, 70, 100, 113, 143 (confirmed by $NH_3$-CI).

D: GC/MS m/e 43, 70, 85, 86, 113, 128, 142, ($M^+=157$ by CI).

C: GC/MS, m/e 43, 70, 75, 85, 100, 128, 144, 160 ($M^+=175$ by CI).

B: GC/MS, m/e 43, 61, 70, 85, 89, 100, 114, 144, 158, 174 ($M^+=189$ by CI).

A: GC/MS, m/e 43,`47, 70, 75, 103, 114, 158, 174, 202 ($M^+=203$ by CI).

G: GC/MS, m/e 43, 68, 69, 111 ($M^+=112$ by CI).

(2) In $CH_2Cl_2$: To 1 g of A (7477-38) in 12 mL of $CH_2Cl_2$ was add 0.27 g of XN-1010. The mixture was stirred at room temperature. After 1.5 h less than 1% A remained with D as the major product (88%) by glpc. Minor amounts of N-acetyl-2-hydroxypyrrolidone (F), a broad peak at r.t. $\sim 5.6$ min (1.9 area %) and N-acetyl-2-pyrroline (G), r.t. $\sim 4.74$ min (9.6%) were also formed.

F: GC/MA; m/e 43, 59, 68, 70, 72, 86, 101, 111, 114, 129 (NH$_3$ CI: 70, 77, 112, 129, 145)

(3) Back Isomerization of N-Acetyl-2-methoxypyrrolidine (E). Six mL of the product of (2) above was diluted with 2 mL of MeOH and catalyzed with 0.13 g of XN-1010. After 1 h at room temperature E decreased from 90.8 to 77.2% and C (acetamidobutyraldehyde dimethyl acetal) increased from less than 1% to 4.9%. The other major product was G (14.2%).

(4) Reaction of N-Acetyl-4-aminobutyraldehyde diethyl acetal (A) with 2,4-Pentandiol. One g of A and 0.51 g of 2,4-pentandiol (epimeric mix) were heated in 1 g of H$_2$O with p-toluenesulfonic acid (10 mg at 50° C./1 h, then an additional 10 mg at 70° C. for 2.5 h). An aliquot was neutralized with KOH/EtOH, extracted with H$_2$O and CH$_2$Cl$_2$ (2× each), back extracted with brine and concentrated. Glpc analysis showed two major product peaks (8.34 and 8.71 min). The 'H NMR as consistent with a mixture of epimeric cyclic 2,4-pentandiol acetals of A.

'H NMR (CDCl$_3$): $\delta$6.11 (br s, 1, NH), 4.86 (low t) 4.56 (br t, ~1, CHO$_2$), 4.3-3.85 (series of m, ~1), 3.71 (m, ~2, CHO), 3.48 (q, imp.), 3.24 (m, 2+, NCH$_2$), 1.96 (s, 3, CH$_3$), 1.7-1.3 (m, ~6, CH$_2$), 1.21 (m, 6+imp., CH$_3$).

(5) Reaction of N-Acetyl-2-methoxypyrrolidine (E) with 2,4-Pentandiol. One g of N-acetyl-2-methoxypyrrolidine (largely E plus lesser an amounts of B, C and D), 0.9 g of 2,4-pentandiol and 240 mg of N-methyl-2-pyrrolidone internal standard were heated at 50°-55° C. in 1 mL of H$_2$O. A separate sample was heated in 1 mL of EtOAc. Results in both samples were similar: rapid initial formation of a small peak at 8.02 min (cyclic hemiamidal of the diol?), followed by growth of major product peaks at 8.35 and 8.73 min, the epimeric cyclic acetals. Small quantities of dehydrated product G (r.t.=4.75 min), and in the aqueous sample, N-acetyl-2-hydroxypyrrolidine, F (before A at ~5.6 min) were also produced. One of the diols appeared to react faster and to a greater extent than the other. Measurements at 3-4 hr were close to the overnight values: ~87% conversion of A, 60-70% of B and essentially quantitative conversion of C and D.

EXAMPLE 14

Additional AEP Derivatives

Three analogs of N-acryloyl-5-ethoxy pyrrolidine (AEP) were prepared similarly to Examples 2 and 3 using the appropriate alcohol or water according to the following reaction scheme:

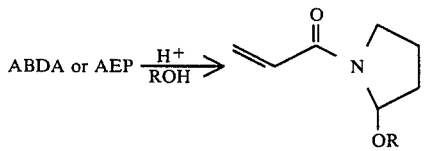

ABDA or AEP $\xrightarrow[\text{ROH}]{\text{H}^+}$

AMP (R = Me)
AiPP (R = iPr)
AHP (R = H)   N—acryloyl-5-hydroxypyrrolidine
AMP (R = Me)  N—acryloyl-5-methoxypyrrolidine
AiPP (R = iPr) N—acryloyl-5-i-propoxypyrrolidine

EXAMPLE 15

The following additional dialkyl acetal monomers were prepared:

(a) N-(2,2-diethoxyethyl)-N'-(2-methacryloxy)ethyl urea (DEEMU)

DEEMU is an example of a methacrylate moiety and a heteroatom in the organic carbonyl radical which radical renders the nitrogen atom electron deficient.

A mixture of 50 mL of CH$_2$Cl$_2$ and 13.3 g (0.1 mol) of aminoacetaldehyde diethyl acetal was cooled to 10°-15° and 14.7 g (0.095 mol) of isocyanatoethyl methacrylate (ICEM) was added at a rate to maintain the reaction below 30° C. Stirring was continued for 1 h. Since some ICEM remained, 2 mL of H$_2$O and small amounts of MeOH and stannous octoate were added. The solution was washed two times with 10 mL of brine, mixed with 40 mL of MeOH, dried over MgSO$_4$ and concentrated on a rotary evaporator. The yellow oil, 17 g (62% yield) partially decomposed on gc analysis, but gave the expected nmr.

nmr (CD$_2$Cl$_2$): $\delta$1.2 (t, 6, CH$_3$), 1.9 (s, 3, CH$_3$), 3.2 (t, 2, CH$_2$N), 3.3-3.8 (m, 6, OCH$_2$, NCH$_2$), 4.2 (t, 2, CH$_2$O), 4.5 (t, 1, CH), 4.9 (br.s, 1, NH), 5.1 (brs, 1, NH), 5.6 (m, 1, vinyl), and 6.1 ppm (m, 1, vinyl).

(b) N-(4,4-diethoxybutyl)-N'-methacryloxyethyl urea (DEBMU)

DEBMU is another example of a monomer of the invention incorporating a methacrylate moiety as part of the olefinically unsaturated radical that renders the nitrogen atom electron deficient.

To 100 mL of CH$_2$Cl$_2$ and 32.2 g (0.2 mole) of 4-aminobutyraldehyde diethyl acetal cooled to 10°-15° C. was added 29.6 g (0.19 mol) of isocyanatoethyl methacrylate at a rate slow enough to maintain the temperature below 30° C. The solution was stirred an additional 1 h, then washed two times with 10 mL of brine, diluted with 50 mL of MeOH, dried over anhydrous MgSO$_4$ and concentrated on a rotary evaporator. The product (60 g, 99% yield) was stabilized with MEHQ. This product degraded significantly on attempted gc analysis (major peak at 10 min rt).

nmr (CD$_2$Cl$_2$): $\delta$1.2 (t, 6, CH$_3$), 1.3-1.8 (m, 4, CH$_2$CH$_2$), 1.9 (d, 3, CH$_3$), 3.2 (q, 2, CH$_2$N), 3.3-3.7 (m, 6, CH$_2$N, CH$_2$O), 4.2 (t, 2, CH$_2$O), 4.4 (t, 1, CH), 5.0 (br.t, 1, NH), 5.1 (br.t, 1, NH), 5.6 (m, 1, vinyl), 6.1 ppm (m, 1, vinyl).

(c) Acrylamidopentanaldehyde diethyl acetal (APDA)

APDA illustrates the next higher analog of ABDA.

(i) Synthesis of Cyanobutyraldehyde Diethyl Acetal.

A mixture of 50 g (0.51 mol) of 4-cyanobutyraldehyde, 100 mL of heptane, 100 mL of absolute EtOH and 1 g of Rohm and Haas XN-1010 strong acid macroreticular cation exchange resin where heated and the water-heptane azeotrope was separated in a Dean Stark trap. No further H$_2$O distilled over after 49 mL of H$_2$O had collected. The trap was replaced with a soxhlet extractor containing 3 A molecular sieving zeolites, and heating was continued for 3 h. The supernatant was concentrated over solid Na$_2$CO$_3$ and distilled on a kugelrohr apparatus from solid Na$_2$CO$_3$ (90° C. bath, 0.05 torr). The product (68 g, 78.4% yield) was 97% of a single component by gc (r.t. 5.24 min).

nmr (CD$_2$Cl$_2$): $\delta$1.16 (t, 6, J=7.0 Hz, CH$_3$), 1.7 (m, 4, CH$_2$CH$_2$), 2.3 (m, 2, NCCH$_2$), 3.4-3.7 (m, 4, CH$_2$) and 4.45 ppm (m, 1, CH).

ir (film): 2250, 1130, 1070 cm$^{-1}$.

(ii) Synthesis of 5-Aminopentanal Diethyl Acetal.

A 500 mL Paar shaker bottle was charged with 48 g of cyanobutyraldehyde diethyl acetal (0.28 mol), 250 mL of EtOH (saturated with NH$_3$) and approximately 15 g of active W. R. Grace Raney nickel catalyst. The system was purged 2 times with $N_2$ and 3 times with $H_2$. The shaker was turned on and reaction initiated at 50 psia and room temperature using a 4 L $H_2$ reservoir which was repressurized twice over 6 h. Approximately 0.66 mol $H_2$ was consumed. The product was filtered, concentrated (41 g) and distilled (92° C., 10 torr) to yield a material with essentially the same gc retention time as the starting material (5.03 min), but no nitrile by ir.

nmr ($CD_2Cl_2$): $\delta$1.15 (~t, 8, $CH_3+NH_2$), 1.39 (m, 4, $CH_2CH_2$), 1.56 (m, 2, $CH_2$), 2.63 (t, 2, $NCH_2$), 3.35–3.7 (m, 4, $CH_2O$), and 4.41 ppm (t, 1, CH).

ir (film): 3600–3100 (vbr), 1130, 1070 $cm^{-1}$.

(iii) Synthesis of Acrylamidopentanal Diethyl Acetal (APDA).

This compound was made from 25 g (0.14 mol) of aminopentanal diethyl acetal, 12.9 g of acryloyl chloride, 35 g of 14N NaOH and 65 mL of $CH_2Cl_2$ using the same procedures as for ABDA (no pH adjustment). The product (32.5 g) had a gc retention time of 7.80 min.

nmr ($CD_2Cl_2$): $\delta$0.91 (t, 6, $CH_3$), 1.05 (m, 2, $CH_2$), 1.40 (m, 4, $CH_2CH_2$), 3.02 (q, 2, $NCH_2$), 3.1–3.45 (m, 4, $OCH_2$), 4.19 (t, 1, CH), 5.31 (m, 1, vinyl), 5.94 (m, 2, vinyl), and 6.50 ppm (br.s. 1, NH).

(d) N-(4,4-Diethoxybutyl)-O-vinylcarbamate (DBVC)

DBVC is an example of the monomer of the invention containing a vinyl carbamate moiety.

This procedure is essentially the same as that for ABDA. To 95 mL of $CH_2Cl_2$ and 50 g of 14N NaOH in a 500 mL flask cooled to 10° C. was added 37.8 g (0.235 mol) of 4-aminobutyraldehyde diethyl acetal. The mixture was stirred vigorously while vinyl chloroformate, 25 g (0.235 mol), was added at a rate to maintain the reaction below 30° C. One hour after the addition was complete, the reaction was monitored by gc, showing complete consumption of the amine. The final pH was 10.3. The phases were separated. The organic phase was washed with saturated aqueous NaCl, and the aqueous phase was back extracted with fresh $CH_2Cl_2$. The combined organic phases were dried over anhydrous $MgSO_4$ and concentrated on a rotary evaporator to yield 34.5 g (63.5% yield) of a product analyzing as 98% a single peak at 7.13 min. Vacuum distillation of a 4 g sample over $Na_2CO_3$ gave 3.25 g collected at 110°–130° C./0.2 torr. This material had a gc retention time of 5.16 min (decomposition on the gc), but gave a correct nmr ($CD_2Cl_2$): $\delta$1.15 (t, 6, $CH_3$), 1.60 (m, 4, $CH_2CH_2$), 3.18 (q, 2, $NCH_2$). 3.25–3.7 (m, 4, $OCH_2$), 4.36 (d, 1, vinyl), 4.45 (t, 1, CH), 4.67 (dd, 1, vinyl), 5.56 (brs, 1, NH), 7.18 (dd, 1, vinyl).

(e) Crotonamidobutyraldehyde diethyl acetal (CBDA)

CBDA is an example of a monomer of the invention containing the crotonamide moiety having the olefinic unsaturation.

This reaction was run as with DBVC (Example 15d) with 80.5 g (0.5 mol) of AmBDA, 52.2 g of crotonoyl chloride, 200 mL of $CH_2Cl_2$ and 100 g of 14N NaOH. The final product was adjusted to pH 10.5 with dilute HOAc and worked up as above to yield 97 g of clear yellow oil. By gc, 88% of the total had a retention time of 4.46 min. Kugelrohr distillation of 5 g gave 4.95 g of lighter colored product at 150°–160° C. bath temperature (0.22 torr), nmr ($CD_2Cl_2$): $\delta$: 1.17 (t, 6, $CH_3$), 1.59 (m, 4, $CH_2CH_2$), 1.82 (dm, 3, $CH_3C=$), 3.25 (m, 2, $NCH_2$), 3.35–3.7 (m, 4, $OCH_2$), 4.43 (~t, 1, CH), 5.84 (dm, 1, vinyl), 6.31 (bs, 1, NH) and 6.73 ppm (dq, 1, vinyl).

(f) Cinnamidobutyraldehyde diethyl acetal (DEBC)

DEBC is an example of a cinnimamide moiety containing polymerizable monomer of the invention.

Cinnamoyl chloride, 55 g (0.33 mol) was added slowly to a cooled two phase mixture of aminobutyraldehyde diethyl acetal, 53.1 g (0.33 mol), 132 mL of $CH_2Cl_2$ and 65 g of 14N NaOH. The product partly precipitated from $CH_2Cl_2$. Work-up (aqueous phase separation, back extraction with $CH_2Cl_2$, concentration at low pressure) gave 110 g of a crude solid, mp 45°–47° C. showing as the major product (>90%) by gc a compound at 9.16 min. Attempted kugelrohr distillation produced sample decomposition above 200° C.

nmr (DMSO-$d_6$): $\delta$1.10 (t, 6, $CH_3$), 1.50 (m, 4, $CH_2CH_2$), 2.50 (sh. m, DMSO-$d_5$), 3.16 (~t, 2, $CH_2N$), 3.3–3.6 (m, 4, $CH_2O$), 4.44 (~t, 1, CH), 6.64 (d, 1, J=16 Hz, vinyl) and 7.2–7.6 ppm (m, 6, vinyl and aromatic).

ir (solid film): 3270, 1655, 1620, 1550, 1455, 1345, 1230, 1130, 1065 $cm^{-1}$.

(g) N-allyl-N'-(diethoxyethyl)urea (ADEEU)

ADEEU is a monomer according to the invention which contains a urea moiety and can be cyclized by acidic cure to a 5-membered cyclic urea.

Allylisocyanate (16.6 g, 0.2 mol) was added slowly to a rapidly stirred ice cooled two-phase mixture of 26.6 g (0.2 mol) of aminoacetaldehyde diethyl acetal, 70 mL of $CH_2Cl_2$ and 40 g of 14N NaOH. A small additional sample of isocyanate was postadded to complete amine conversion. Work-up as for ABDA and concentration over $Na_2CO_3$ gave 32.2 g (80% yield) of a product composed 99.5% of a single peak at retention time 7.83 min.

nmr ($CD_2Cl_2$): $\delta$1.18 (t, 6, $CH_3$), 3.23 (t, 2, $CH_2N$), 3.8–3.4 (m, 4, $OCH_2$), 3.73 (m, 2, allyl), 4.45 (t, 1, CH), 5.06 (dm, 1, J=10 Hz, vinyl), 5.15 (dm, J~18 Hz, vinyl), 5.66 (br.t, 1, NH) and ~5.8 ppm (m+br.t, 2, NH, vinyl).

ir (film): 3340, 1635, 1570, 1260 (br), 1130, 1060 $cm^{-1}$.

(h) Acrylamidobutyraldehyde dimethyl acetal (ABDA-Me)

ABDA-Me is the dimethylacetal derivative of ABDA.

(i) Synthesis of Aminobutyraldehyde Dimethyl Acetal (AmBDA-Me).

This reaction was run as for aminopentanal diethyl acetal [Example 15(c)(ii)] using MeOH as solvent (160 mL), 7.8 g of Raney nickel and 25 g (0.194 mol) of cyanopropionaldehyde dimethyl acetal. ($H_2$ consumption 113% of theoretical after 3.5 hr.). The product after concentration at reduced pressure analyzed as an essentially pure single component at 3.40 min by gc (20 g, 77.5% yield).

nmr ($CD_2Cl_2$): $\delta$1.05 (s, 2, $NH_2$), 1.3–1.7 (2 m's, 4, $CH_2CH_2$), 2.64 (t, 2, $CH_2N$), 3.26 (s, 6, $CH_3$), and 4.32 ppm (~t, 1, CH).

ir (film): 3360 (s, br), 3300 (s, br), 1600 (m, br), 1450 (s), 1375 (d, s), 1125 (s), 1060 (s, br), no CN at 2250 $cm^{-1}$.

(ii) Synthesis of Acrylamidobutyraldehyde Dimethyl Acetal (ABDA-Me).

Using the standard procedure for ABDA-Et, 16.5 g (0.124 mol) of the above aminobutyraldehyde dimethyl acetal was reacted with 11.2 g (0.124 mol) of acryloyl chloride in 40 mL of $CH_2Cl_2$/30 g of 14N NaOH. The product mixture was adjusted to pH 10.0 and worked up as usual to yield 16 g of oil showing predominantly a single component by gc at 7.00 min.

Anal. Calc'd for $C_9H_{17}NO_3$; C, 57.73; H, 9.15; N, 7.47; Found: C, 57.54; H, 9.26; N, 7.35.

nmr ($CD_2Cl_2$): δ1.59 (m, 4, $CH_2CH_2$), 3.29 (s+m, 8, $CH_3$, $NCH_2$), 4.33 (~t, 1, J~5.3 Hz, CH), 5.58 (dd, 1, J=3.1 Hz, J=8.4 Hz, vinyl), 6.11 (~dd, 1, J=16.9 Hz, J=8.4 Hz, vinyl), 6.18 (~d, J=3.1 Hz, J=16.9 Hz, vinyl) and 6.3 ppm (br, 1, NH).

ir (film): 3295, 1660, 1625, 1550, 1135, 1060 (br) cm$^{-1}$.

(i) N-vinylsulfonyl-2-ethoxypyrrolidine (VSEP).

To a vigorously stirred mixture of 25.7 g (0.158 mol) of 2-chloroethanesulfonyl chloride in 100 mL of $CH_2Cl_2$ was slowly added a mixture of 25.4 g (0.158 mol) of aminobutyraldehyde diethyl acetal, 35 g (0.34 mol) of triethylamine and 50 mL of $CH_2Cl_2$. The temperature was maintained below 10° C. Stirring was continued for 2 h. The solution was filtered to remove solid $Et_3NHCl$ and extracted with 10 mL of 10% HCl (pH 3.0), then 10 mL of 4% $NaHCO_3$. The organic layer was dried with $MgSO_4$ and concentrated on a rotary evaporator to yield 25.7 g of brown liquid containing one major and one significant minor component by gc (~78% at 10.83 min, 8% at 9.12 min). Distillation of an aliquot on a kugelrohr apparatus (130° C., 0.5 torr) increased the ratio of the short retention time peak.

nmr ($CD_2Cl_2$, undistilled) δ1.19 (t, 3, $CH_3$), 1.5-2.2 (m 4, $CH_2CH_2$), 3.8-3.1 (m, 4, $OCH_2$, $NCH_2$), 5.03 (d, 1, J=4.5 Hz, NCHO), 5.96 (d, 1, J=9.5 Hz, vinyl), 6.19 (d, 1, J=16.4 Hz, vinyl), and 6.47 ppm (dd, 1, J=9.5 Hz, J=16.4 Hz, vinyl).

ir (film); no NH, 1345 (s), 1165 (s), 1012, 735 cm$^{-1}$.

(j) 1-Allyl-6-ethoxy-4-methylhexahydropyrimidin-2-one (AEMHP).

Following a related procedure, [G. Zigeuner, W. Rauter, *Monatshefte fur Chemie*, 96, 1950 (1965)], allylurea (24.5 g, 0.25 mol), crotonaldehyde (19.67 g, 0.29 mol) and 37% HCl (12 drops) were mixed with 140 g of EtOH at room temperature for 3 d, during which all of the crotonaldehyde was consumed. The major product had a retention time near that of allylurea. The dark mixture was neutralized with $Na_2CO_3$, filtered and concentrated at reduced pressure. Part of the crude mixture was extracted with cyclohexane, decolorized with charcoal, filtered and concentrated to give a light yellow oil which produced white crystals (mp 72°-76° C.) on standing. A separate sample was submitted to kugelrohr distillation (0.05 torr) to give further products: E at 90° C., F at 145°-155° C. (solid, mp 72°-76° C.) and G at 145°-155° C. (liquid).

nmr ($CD_2Cl_2$): δ1.16 (d, 3, J=6.5 Hz, $CH_3$), 1.18 (t, 3, J=6.8 Hz, $CH_3$), 1.45 (ddd, 1, J=13.7 Hz, J=12.1 Hz, J=2.9 Hz, CHH'), 2.01 (dm, 1, J=13.7 Hz, J~2.4 Hz, CHH'), 3.49 (q, 1, J=6.7 Hz, CHH'O), 3.50 (q, 1, J=6.7 Hz, CHH'O), 3.8-3.5 (m, 2, CHN, allyl), 4.38 (ddt, 1, J=18.0 Hz, J=4.4 Hz, J~1.7 Hz, allyl), 4.49 (t, 1, J~2.6 Hz, NCHO), 4.81 (br.s, 1, NH), 5.08 (t, 1, J~1.7 Hz, vinyl), 5.14 (dq, 1, J=6.1 Hz, J~1.4 Hz, vinyl), and 5.80 ppm (m, 1, vinyl). Sample E was similar, but contained more signals, indicating a mixture of epimers.

ir (8074-15, solid film): 3200 (br), 1640, 1505, 1425 (br), 1350 cm$^{-1}$.

(k) N-Allyl-N'-Butyraldehyde Diethyl Acetal Melamines and Ammelines.

The example demonstrates the preparation of melamine derivatives. Cyanuric chloride, 18.4 g (0.1 mol) was dissolved in 125 ml of $CH_2Cl_2$ and added to 300 ml of ice/water and stirred mechanically. Allylamine, 5.7 g (0.1 mol), in 100 ml of $H_2O$ containing 10.6 g (0.1 mol) of $Na_2CO_3$ was added over 30 min while maintaining a 0°-5° C. temperature range. Allylamine conversion was complete by gc. At the same temperature 32.2 g (0.2 mol) of aminobutyraldehyde diethyl acetal in 150 ml of water containing 21 g (0.2 mol) of $Na_2CO_3$ was added. The mixture warmed to room temperature over 90 min and was then heated at reflux for 2 h, but amine conversion remained incomplete. The reaction mixture was separated and the aqueous layer was back extracted with $CH_2Cl_2$. The combined organic fractions were concentrated under reduced pressure to give a white solid. This was recrystallized, giving 43 g of fraction 1, mp 153°-154° C., from MeOH and 0.7 g of fraction 2, mp 143°-144° C., from hexane.

nmr ($CD_2Cl_2$) fxn 1: δ1.07 (2t, 6, $CH_3$), 1.66 (m, ~5, $CH_2$, OH?), 3.7-3.3 (m, 6, $OCH_2$, $NCH_2$), 4.04 (m, 2, allyl), 4.47 (m, 1, CH), ~5.21 (dm, 1, J~18 Hz, vinyl), ~5.14 (dm, 1, J~12 Hz, vinyl), ~5.4, 5.6, 5.8 (br.m's, 1-2, NH), and ~5.9 (m, ~1, vinyl).

fxn 2: identical chemical shifts, integral ratios approximately 6:4.6:6:1.1:0.9:1.4:2 (δ5.4–6.0).

ir (solid film): 3250 (br), 3090 (br), 1638, 1550 (s), 1409, 1130, 1105, 1065 (br), 990, 802 cm$^{-1}$.

Fraction 1 is most likely the Ammeline 1 and 2 probably contains 1 and the desired 2. The presence of both an allyl and an amine/blocked aldehyde is clear, however.

GC Analysis

Most gas chromatographic analyses were done on a Hewlett-Packard 5380 gas chromatograph using a 42 ft and a 12 m OV-101 capillary column, split ratio 200:1, column flow approximately 1 ml/min and using the following programs:

a. 65°/2 min, then 65→250° at 25°/min
b. 150°/2 min, then 150Δ250° at 15°/min
c. 65°/2 min, then 65→250° at 15°/min
d. 70°/2 min, then 70→250° at 15°/min
e. 150°/2 min, then 150→300° at 15°/min.

A few runs were also done on a 30 m wide bore DB-5 (60:1 split ratio) or a 30 m DB-17 column.

EXAMPLE 16

Vinyl Acetate/Ethylene/ABDA (6%) Emulsion Polymer Synthesis, Continuous Comonomer Addition A 1 gal reactor was charged with 42.8 g of vinyl acetate, 14.3 g of Igepal CO-887, 10.0 g of Igepal CO-630, 10.0 g of Pluronic F-68, 10.0 g of Pluronic L-64, 857 g of a 2% aqueous solution of Natrosol 250 GR, 47.0 g of deionized water, 4.1 g of sodium acetate, 0.05 g of ferric ammonium sulfate, 3.02 g of acetic acid, and 11.4 g of a 10% aqueous solution of sodium formaldehyde sulfoxylate (SFS) and purged for 40 min with nitrogen. The mixture was heated to 48° C., agitated at 800 RPM, pressurized with ethylene to 450 psi and initiated by adding a solution of 14 g of potassium persulfate and 47 g of sodium acetate in 981.3 g of water at 0.6 mL/min. Upon initiation, the rate of catalyst addition was switched to automatic control and 984.7 g of vinyl acetate was added at 6.3 mL/min and 370 g of a 20% aqueous solution of ABDA was added at 1.8 mL/min. One hour after the start of catalyst addition, a 10% aqueous solution of SFS was pumped in at 0.2 mL/min. The reaction temperature was maintained at 49° C. and the pressure at 460 psi. After three h the vinyl acetate had been added and the ethylene makeup was shut off. Thirty min later the ABDA had been added. The catalyst and activator solutions were added for an additional 30 min. The reaction was cooled, degassed and treated with 5 g of a 10% aqueous solution of t-butyl hydroperoxide and 4.6 g of a 50% aqueous solution of colloid defoamer. The resulting emulsion had 44.4% solids, pH 4.52 and a viscosity of 1080 cps.

EXAMPLE 17

PVOH/g-VAc/ABDA (19/76/5 Ratio), Continuous Functional Comonomer Addition

A 2 L reactor was charged with 300 g of a 20% aqueous solution of PVOH (Vinol 205), 210 g of deionized water and 15 g of vinyl acetate and purged for 45 min with nitrogen. The kettle was heated to 55° C. and the reaction was initiated by adding two solutions (one a 2.5% aqueous solution of hydrogen peroxide and the other a 2.5% aqueous solution of ascorbic acid) at a rate of 0.34 mL/min. Upon initiation, a solution of of 15 g ABDA in 225 g of vinyl acetate was added at a rate of 2.5 mL/min. The jacket was cooled to maintain a reaction temperature of 56° C. A free monomer level of 1.3% was maintained. The reaction was complete after 2.25 h to give a 37% solids emulsion, pH 5.43, viscosity 11,640 cps.

EXAMPLE 18

PVOH/g-VAc/ABDA, (19/76/5 Ratio), Comonomer Addition at the End

A 2 L reactor was charged with 300 g of a 20% aqueous solution of Vinol 205, 210 g of deionized water, and 225 g of vinyl acetate and purged for 45 min with nitrogen. The kettle was heated to 55° C. and the reaction was initiated by adding two solutions (one a 2.5% aqueous solution of hydrogen peroxide and the other a 2.5% aqueous solution of ascorbic acid) at a rate of 0.34 mL/min. Upon initiation, the activator and catalyst addition rates were reduced to 5.5 mL/h. The jacket was cooled to maintain a reaction temperature of 56° C. When the free monomer reached 2.0%, a mixture of 15 g of ABDA and 15 g of vinyl acetate was added at a rate of 2.3 mL/min. The reaction was complete after 1.25 h to give a 35.4% solids emulsion, pH 5.32, and viscosity 2160 cps.

EXAMPLE 19

PVOH/g-VAc/ABDA (19/76/5 Ratio), Trail Addition of Comonomer

A 2 L reactor was charged with 300 g of a 20% aqueous solution of Vinol 205, 210 g of deionized water and 15 g of vinyl acetate and purged for 45 min with nitrogen. The kettle was heated to 55° C. and the reaction was initiated by adding two solutions (one a 2.5% aqueous solution of hydrogen peroxide and the other a 2.5% aqueous solution of ascorbic acid) at a rate of 0.34 mL/min. Upon initiation the activator and catalyst addition were slowed to 5.5 mL/h and 30 g of vinyl acetate was added at 2.15 mL/min. When the vinyl acetate had been added, a mixture of 2.65 g of ABDA in 195 g of vinyl acetate was added at 2.15 mL/min. When this had been added, 11.8 g of a 20% aqueous solution of ABDA was added at the same rate. The jacket was cooled to maintain a reaction temperature of 55° C. The free monomer level was maintained at approximately 0.8%. The reaction was complete in 1.5 h. Solids: 34.4%, pH: 4.81, viscosity: 3800 cps.

EXAMPLE 20

VAc/ABDA (90/10), Continuous Comonomer Addition

A 2 L reactor was charged with 30 g of vinyl acetate, 200 g of a 2% aqueous solution of Natrosol 250 GR, 3.08 g of Igepal CO-887, 2.16 g of Igepal CO-630, 2.16 g of Pluronic F-68, 21.6 g of Pluronic L-64, and 272 g of deionized water and purged for 45 min with nitrogen. The kettle was heated to 55° C. and the reaction was initiated by adding two solutions (one a 2.5% aqueous solution of hydrogen peroxide and the other a 2.5% aqueous solution of ascorbic acid) at a rate of 0.34 mL/min. Upon initiation, the activator and catalyst addition rates were slowed to 5.5 mL/h and a mixture of 30 g of ABDA in 240 g of vinyl acetate was added at 2.15 mL/min. The jacket was cooled to maintain a reaction temperature of 55° C. and the free monomer was maintained at about 1.4%. The reaction was complete in 1.5 h. Solids: 33.3%, pH: 2.98, viscosity: 860 cps.

EXAMPLE 21

PVOH/g-VAc/E/ABDA 9/86/E/5 Ratio Emulsion Polymer Synthesis, Continuous Comonomer Addition A 1 gal reactor was charged with 1520 g of a 10% aqueous solution of Vinol 205, 283 g of vinyl acetate, 10 g of a 0.2% aqueous solution of ferrous sulfate and 10 g of a 2.5% aqueous solution of erythorbic acid and purged for 30 min with nitrogen. The kettle was heated to 53° C., agitated at 900 RPM, pressurized with ethylene to 900 psi (no makeup) and initiated by adding two solutions (one a 2.5% aqueous solution of erythorbic acid and the other a 2.5% aqueous solution of hydrogen peroxide) at 3.0 mL/min. Upon initiation, the catalyst and activator flow were slowed to 0.7 mL/min.

Vinyl acetate (1130 g) was added at 3.8 mL/min and 394 g of a 20% aqueous solution of ABDA (with 2.0 g of Igepal CO-887 added) was added at 1.3 mL/min. The temperature was maintained at 53° C. and the free monomer at 4%. The monomers were added over 4.5 h. The catalyst and activator additions were continued for an additional 30 min. The reaction was cooled, degassed and treated with 4.6 of a 50% aqueous solution of Colloid 585. Solids: 41.1%, pH: 3.6, viscosity: 5740 cps.

EXAMPLE 22

PVOH/g-VAc/E/ABDA (9/86/E/5 Ratio), Comonomer Addition at the End

A 1 gal reactor was charged with 1,414 g of a 10% aqueous solution of Vinol 205, 263 g of vinyl acetate, 10 g of a 0.2% aqueous solution of ferrous sulfate and 10 g of a 2.5% aqueous solution of erythorbic acid and purged for 30 min with nitrogen. The mixture was heated to 55° C., agitated at 900 RPM, pressurized with ethylene to 900 psi (no makeup) and initiated by adding two solutions (one a 2.5% aqueous solution of erythorbic acid and the other a 2.5% aqueous solution of hydrogen peroxide) at 3.0 mL/min. Upon initition, the catalyst and activator rates were slowed to 0.70 mL/min and 1051 g of vinyl acetate was added at 3.8 mL/min. The temperature was maintained at ~53° C. and the free monomer at 4.0%. After 4.25 h, 366 g of a 20% aqueous solution of ABDA was added at 4.1 mL/min. The vinyl acetate delay was complete after five h and the ABDA delay after 5.5 h. The activator and catalyst solutions were added until the 6 h mark, whereupon the reaction was cooled, degassed and treated with 4.6 g of a 50% aqueous solution of Colloid 585. Solids: 41.8%; pH: 3.12, adjusted to 4.2; viscosity: 17,760 cps.

EXAMPLE 23

VAc/EBDA (6%)Emulsion Polymer, Comonomer Added at the End

A 1 gal reactor was charged with 42.8 g of vinyl acetate, 14.3 g of Igepal CO-887, 10.0 g of Igepal CO-630, 10.0 g of Pluronic F-68, 10.0 g of Pluronic LC-64, 857 g of a 2% aqueous solution of Natrosol 250 GR, 4.1 g of sodium acetate, 3.30 g of acetic acid, 0.05 g of ferric ammonium sulfate, 47.0 g of deionized water and 11.4 g of a 10% aqueous solution of SFS, and purged for 40 min with nitrogen. The mixture was heated to 48° C., agitated at 800 RPM, pressurized with ethylene to 450 psi (continuous makeup) and initiated by adding a solution of 14 g of potassium persulfate and 4.7 g of sodium acetate in 981 g of water at 0.6 mL/min. Upon initiation, the catalyst addition rate was switched to automatic control and 985 g of vinyl acetate was added at 6.3 mL/min. One h after the start of the catalyst addition, a 10% aqueous solution of SFS was pumped in at 0.2 mL/min. The reaction temperature was maintained at 48° C. and a 5° difference was maintained between the reactor and jacket temperatures. The free monomer was held at 5%. After 2.25 h, 370 g of a 20% aqueous solution of ABDA was added at 3.5 mL/min. The vinyl acetate delay was complete at 3.0 h and the ethylene makeup was then turned off. The ABDA delay was complete at 4.0 h, whereupon the free monomer was 1.5%. The reaction was cooled, degassed and treated with 5 g of a 10% aqueous solution of t-butyl hydroperoxide and 4.6 g of a 50% aqueous solution of Colloid 585. Solids: 45.8%, pH: 4.37, viscosity: 2,320 cps.

EXAMPLE 24

PVOH/g-VCl/E/ABDA (4.7/76/17.4/1), Continuous Comonomer Addition

The polymerization was carried out in a 1 gal pressure vessel equipped with a jacket and an agitation system involving turbine blades. In preparing the copolymer emulsion the following initial charge was introduced into the reaction vessel:

| INITIAL CHARGE | |
|---|---|
| Distilled Water | 555 g |
| Ferrous Ammonium Sulfate | 0.9 g |
| Sequestrine 30A[a] | 2.7 g |
| Vinol 205[b] PVOH (12% Solution) | 854 g |

[a]Ethylenediamine tetraacetic acid sodium salt.
[b]An 87 to 89 mole % hydrolyzed PVOH marketed by Air Products and Chemicals, Inc.

The pH of the above charge was adjusted between 4.0 and 4.5 with acetic acid. The vessel contents were agitated at 200 rpm and purged three times with ethylene (25 psig). Vinyl chloride monomer (240 g) was then added and the reactor was heated to 55° C. and pressurized with ethylene (875 psig). The agitation was increased to 900 rpm and 7 mL of a 10% aqueous solution of erythorbic acid (pH 4.5) was pumped into the reactor. After the temperature and pressure had equilibrated, the polymerization was initiated with a 1% aqueous hydrogen peroxide solution. After the heat of polymerization output rate began to decrease, the remaining vinyl chloride monomer (1,415 g) and 105 g of a 20% aqueous solution of ABDA (plus 1 g of Igepal CO887 surfactant) were added over a 4 h and a 4¾ h period respectively, maintaining the polymerization temperature of 55° C. using approximately 1.2 g hydrogen peroxide as a 1% solution and 2.7 g erythorbic acid as the activator. Additional oxidant and reductant were used after the vinyl chloride monomer had been added to complete the polymerization. A total of 1.67 g of hydrogen peroxide as a 1% solution and 5.0 g of erythorbic acid were used for the entire polymerization. The ethylene pressure was allowed to "float" during the polymerization without makeup or withdrawal.

The emulsion was transferred to a degasser and the unreacted vinyl chloride monomer reduced to less than 10 ppm by the addition of vinyl acetate (15 g) followed by t-butyl hydroperoxide (4 g) and erythorbic acid (3 g), ferrous ammonium sulfate (0.2 g) and sequestrine 30A (0.8 g) in water (50 g). The vinyl chloride-ethylene copolymer was 76 wt. % vinyl chloride, 17.4 wt. % ethylene, 0.96% ABDA and had a Tg of 18.5° C. Emulsion solids were 52%, $[\eta]=0.41$ (soluble portion).

EXAMPLE 25

Vinyl Acetate/Butyl Acrylate Emulsion Polymerizations

An atmospheric emulsion polymerization was performed in a 1 L resin kettle outfitted with a double propeller agitator and reflux condenser as follows:

Kettle Charge 319 g $H_2O$
0.375 g Natrosol 250 HR
9.2 g Igepal CO-887
2.15 g Igepal CO-630
0.166 g sodium formaldehyde sulfoxylate (SFS)
2.8 g 0.15% $FeSO_4.7H_2O$

Monomer Delay 344 g vinyl acetate
56 g butyl acrylate
7.8 g Pluronics F-68
5.14 g Pluronics L-64
0.58 g t-butylhydroperoxide (TBHP, 70%), Additional TBHP was added to keep the reaction going when necessary.
24 g (3%) comonomer

Activator 0.628 g SFS
0.628 g sodium benzoate
dilute to 25 mL with $DIH_2O$

Chaser 0.25 g t-BHP
0.75 g $DIH_2O$

The $DI-H_2O$ was charged to the kettle and sparged with $N_2$ for 30 min under moderate agitation. The remainder of the kettle charge was added and the mixture was heated to 65° C. Stirring speed was adjusted to give a strong vortex. Each delay was set to run for 2 h. The monomer delay rate was approximately 3.5 mL/min and the activator rate was approximately 0.21 mL/min, but high enough to maintain an excess of activator. The reaction was initiated by pumping in the monomer delay. When the kettle charge became bluish white (within 10 min), the activator was turned on. The temperature was held at 65°–70° C. during the run. Percent free monomer was measured at hourly intervals by KBrO$_3$ titration. After all of the monomer delay had been added and the percent unreacted VAc fell below 1%, the chaser was added to bring the VAc down to ≦0.5%. The vinyl acetate/butyl acrylate/3% ABDA copolymer emulsion had a pH 5.6 and 50% solids.

EXAMPLE 26

VAc/ABDA (90/10) Continuous Comonomer Addition

A 2 L reactor was charged with 30 g of vinyl acetate, 200 g of a 2% aqueous solution of Natrosol 205GR, 3.08 g of Igepal CO-887, 2.16 of Igepal CO-630, 2.16 g of Pluronic F-68, 2.16 g of Pluronic L-64, and 272 g of deionized water and purged for 45 min with nitrogen. The kettle was heated to 55° C. and the reaction initiated by adding two solutions (one a 2.5% aqueous solution of hydrogen peroxide and the other a 2.5% aqueous solution of ascorbic acid) at a rate of 0.34 mL/min. Upon initiation, the activator and catalyst additions were slowed to 5.5 mL/h and a solution of 30 g of ABDA in 240 g of vinyl acetate was added at 2.15 mL/min. The reaction was maintained at a temperature of 55° C. and a free monomer of 1.4%. The reaction was complete in 1.5 h.

EXAMPLE 27

VAc/AEP (90/10) End Comonomer Addition

A 2 L reactor was charged with 542 g of deionized water, 0.37 g of Natrosol 250 HR, 9.2 g of Igepal CO-887, 2.15 g of Igepal CO-630, 2.8 g of aqueous ferrous sulfate heptahydrate (0.15% solution) and 0.16 g of sodium formaldehyde sulfoxylate and purged for 45 min with nitrogen. The kettle was heated to 65° C. and the reaction was initiated by adding a solution of 288 g of vinyl acetate, 5.9 g of Pluronic F-68, 4.1 g of Pluronic L-64 and 0.46 g of t-butyl hydroperoxide (70%) at a rate of 2.8 mL/min. Five min after initiation, a solution of 0.63 g of SFS, 0.63 g of sodium benzoate and 50.5 g of deionized water was added at 0.34 mL/min. When the monomer delay was complete, a solution of 72 g of vinyl acetate, 1.4 g of Pluronic F-68, 1.04 g of Pluornic L-64, 0.12 g of t-butyl hydroperoxide (70%) and 40 g of AEP was added at the same rate. Fifteen min after all the delays had finished a solution of 0.5 g of t-butyl hydroperoxide (70%) in 1.5 g of deionized water was added. The reaction was complete within 30 min.

EXAMPLE 28

VAc/BA/AEP, End Comonomer Addition

A 2 L rector was charged with 542 g of deionized water, 0.37 g of Natrosol 250 HR, 9.2 g of Igepal CO-887, 2.15 g of Igepal CO-630, 0.156 g of sodium formaldehyde sulfoxylate and 2.8 g of aqueous ferrous sulfate heptahydrate (0.15% solution). It was then purged for 45 min with nitrogen. The kettle was heated to 65° C., and the reaction was initiated by adding 330 g of a solution comprised of 344 g of vinyl acetate, 56 g of butyl acrylate, 7.29 g of Pluronic F-68, 5.4 g of Pluronic C-64 and 0.58 g of 70% TBHP at a rate of 2.8 mL/min. Ten min after initiation, a solution of 0.63 g of SFS, 0.63 g of sodium benzoate and 50.5 g of deionized water was added at 0.34 mL/min. When the monomer delay was complete, a solution comprises of 82.6 g of the initial monomer delay and 40 g of AEP was added at the same rate. Fifteen min after the delays had finished, a solution of 0.5 g of TBHP (70%) in 1.5 g of deionized water was added. The reaction was complete within 30 min.

EXAMPLE 29

VAc/BA/AEP, Continuous Comonomer Addition

A 2 L reactor was charged with 542 g of deionized water, 0.37 g of Natrosol 250 HR, 9.2 g of Igepal CO-887, 2.15 g of Igepal CO-636, 0.156 g of SFS and 2.8 g of aqueous ferrous sulfate heptahydrate (0.15% solution). The kettle was purged for 45 min with nitrogen and heated to 65° C. The reaction was initiated by adding a solution of 344 g of vinyl acetate, 56 g of butyl acrylate, 40 g of AEP, 7.2 g of Pluconic F-68, 5.14 g of Pluconic C-64, and 0.58 g of TBHP (70%) at a rate of 2.8 mL/min. Seven min after initiation a solution of 6.63 g of SFS, 0.63 g of sodium benzoate and 50.5 g of deionized water was added at 0.34 mL/min. Fifteen min after all the delays were finished, a solution of 0.5 g of TBHP (70%) in 1.5 g of deionized water was added. The reaction was complete within 30 min.

EXAMPLE 30

VAc/BA/ABDA, Trail Comonomer Addition

This reaction was performed as in Example 28 except that when the first monomer delay was completed, a solution comprised of 82.6 g of the initial monomer delay and 20 g of ABDA was added at the same rate, followed by 9.5 g of pure ABDA. Fifteen min after all of the delays had been added, a solution of 0.5 g of TBHP (70%) in 1.5 g of deionized water was added. Reaction was complete within 30 min.

EXAMPLE 31

BA/MMA/ABDA

A 2 L reactor was charged with 752 g of deionized water and 48 g of Triton X-200 purged for 45 min with nitrogen. A solution of 191 g of butyl acrylate, 169 g of methyl methacrylate (MMA), 40 g of ABDA, 8 g of aqueous ferrous sulfate heptahydrate (0.15% solution) and 2 g of ammonium persulfate was added and the mixture was stirred for 30 min. Then 2.0 g of sodium meta-bisulfite and 10 drops of TBHP (70%) were added. The reaction temperature rose over 12 min to 50° C. and then dropped. When the temperature reached 25° C., the reaction was complete.

EXAMPLE 32

VAc/DBMA, End Comonomer Addition

A 2 L reactor was charged with 468 g of deionized water, 3.08 g of Igepal CO-887, 2.16 g of Igepal CO-630, 2.16 g of Pluronic F-68, 2.19 g of Pluronic C-64, 4.0 g of Natrosol 250 GR and 30 g of vinyl acetate. The kettle was purged for 45 min with nitrogen and heated to 55° C. The reaction was initiated by adding a 2.5% aqueous solution of ascorbic acid and a 2.5% aqueous solution of hydrogen peroxide on demand by temperature. Five min after initiation, 225 g of vinyl acetate was added at a rate of 2.3 mL/min followed by a solution of 15 g of vinyl acetate and 18 g of DBMA. After 4.5 h, the free monomer was less than 1.5% and the reaction was complete.

EXAMPLE 33

VAc/BA/ABDA/BA Chaser

This reaction was a repeat of Example 28 except that the first monomer delay employed only 40 g of butyl acrylate. When the first delay was completed, a solution comprised of 79.4 g of the initial monomer delay and 15 g of ABDA was added at the same rate, followed by 16 g of butyl acrylate. Fifteen min after all the delays had finished, a solution of 0.5 g of TBHP (70%) in 1.5 g of deionized water was added. The reaction was complete within 30 min.

EXAMPLES 34–49

Swell Index and Percent Solubles Measurements on Emulsion and Solution Polymers

Polymer films were cast on Mylar film at 25% solids with various post additives. The films were air dried (16–48 h) then cured for 3 and 10 min at 150° C. A convected oven (oven 1) was used unless otherwise indicated. Oven 2 was not convected. Small samples (50–100 mg) of film were weighed, soaked in dimethylformamide (DMF) for 1 h, briefly, pat-dried and reweighed in an Al weighing pan. The samples were then redried at 150° C. (20 torr) or 170° C., 1 atm for 30 min.

$$\text{Swell index} = \frac{\text{sample weight swollen in } DMF}{\text{original sample weight}}$$

% Solubles =

$$100 \left[ 1 - \left( \frac{\text{weight of dry film after } DMF \text{ swell}}{\text{original dry film weight}} \right) \right]$$

See Table 1A for additional vinyl acetate/ethylene copolymer emulsions prepared generally following the procedure of Example 16.

Table 1B gives additional vinyl acetate/butyl acrylate copolymer emulsions prepared generally following the procedure of Example 25.

Table 2 provides vinyl acetate copolymer emulsions prepared generally following the procedure of Examples 26 or 27.

Tables 1A, 1B and 2 also include swell index and percent solubles data which show that copolymers incorporating the acetal and hemiamidal copolymers of the invention can be cross-linked.

TABLE 1A

VAc/Ethylene Emulsion Polymers

| Example | X-Linker (molarity) | Catalyst | pH | Swell Index (DMF) 3 min cure | 10 min cure | % DMF Solubles 3 min | 10 min | color[2] |
|---|---|---|---|---|---|---|---|---|
| A-105 | 5% NMA (0.5M) continuous[6] | $H_3PO_4$ | 3.0 | 2.9 | 2.9 | 15 | 10 | C |
|  |  | 1% PTSA |  | 2.5 | 2.3 | 7 | 7 | LY |
|  |  | 1% $NH_4Cl$ |  | 4.3 | 4.1 | 8 | 10 | LY |
| 34 | None | 1% PTSA |  | ∞ | ∞ | 100 | 100 | LY |
| 35 | 3% ABDA (0.14M) continuous | $H_3PO_4$ | 3.0 | 15.4 | 15.6 | 24 | 15 | Y |
|  |  | 1% PTSA |  | 8.9 | 6.8 | 11 | 8 | Y |
|  |  | 1% PTSA + 1% PVOH |  | 6.7 | 6.3 | 9 | 9 | Y |
| 36 | 6% ABDA (0.28M) continuous | $H_3PO_4$ | 3.0 | 12.6 | 11.6 | 23 | 17 | Y |
|  |  | $H_3PO_4$ + 1% PVOH | 2.5 | 12.1 | 9.5 | 15 | 11 | LY |
|  |  | 1% PTSA |  | 8.9 | 6.8 | 11 | 8 | Y |
|  |  | 1% $NH_4Cl$ (.19M) |  | 6.2 | 5.8 | 8 | 7 | LY |
|  |  | 1% $NaHSO_4$ | 2.1 | 9.9 | 6.8 | 9 | 6 | Y |
|  |  | 1% Maleic acid | 2.4 | 13.8 | 12.7 | 19 | 18 | LY |
|  |  | 1% $(CO_2H)_2$ | 2.0 | 10.9 | 9.4 | 16 | 12 | Y |
| 37 | 9% ABDA (0.42M) continuous[6] | $H_3PO_4$ | 3.0 | 10.6 | 8.9 | 15 | 12 | Y |
|  |  | 1% PTSA |  | 6.0 | 4.5 | 10 | 8 | Y |
|  |  | 1% PTSA + 2% PVOH |  | 4.7 | 4.1 | 8 | 6 | Y |
| 38 | 6% ABDA (0.28M) End[6] | 1.6% $H_3PO_4$ (oven 2) | 2.5 | 7.0 | 6.1 | 13 | 8 | Y |
|  |  | 1% PTSA (oven 2) |  | 4.5 | 4.5 | 5 | 5 | Y |
|  |  | 1% PTSA + 1% PVOH(oven 2) |  | 4.7 | 4.6 | 6 | 8 | Y |
|  |  | 1% $NH_4Cl$ (0.19M)(oven 2) |  | 4.1 | 3.9 | 10 | 11 | LY |
| 39 | 3% AEP(0.18M) end, ($NH_3$) | 2% PTSA |  | 9.0 | 9.5 | 34 | 25 | Y |
|  |  | 2% $NH_4Cl$ (0.28M) |  | 10.4 | 9.6 | 30 | 23 | Y |
| 40 | 2.5% ADBC (0.1M) cont., Tg + 9 ($NH_3$) | — |  | ∞(218°/1 min) | ∞(218°/1.5 min) | 100 | 100 | LY |
|  |  | 2% PTSA |  | 7.2 | 7.1 | 9 | 7 | DY |
|  |  | 2% $NH_4Cl$ (0.28M) |  | ∞ | ∞ | 100 | 100 | LY |
| 41 | 2.5% ADBC (0.1M) cont. | — |  | 15(218°/1 min) | 13.5(1.5 min) | 21 | 17 | VLY |
|  |  | 1% PTSA |  | 6.9 | 6.7 | 11 | 11 | LY |
|  |  | 2% PTSA |  | 7.7 | 7.0 | 6 | 9 | LY |

TABLE 1B

Vinyl Acetate/Butyl Acrylate Emulsion Polymers

| Example | X-Linker (molarity) | Catalyst | Oven[5] | Swell Index (DMF) 3 min cure[1] | 10 min cure[1] | % DMF Solubles 3 min | 10 min | color[2] |
|---|---|---|---|---|---|---|---|---|
| 42 | 3% BNMA (0.19M) continuous | 1% $NH_4Cl$ | 1 | 4.7 | 4.5 | 9 | 9 | B |
|  |  | 1% $MgCl_2$ | 1 | 4.7 | 4.7 | 9 | 8 | LB |
| 43 | 3% NMA (0.3M) continuous | 1% $NH_4Cl$ | 1 | 2.8 | 2.8 | 8 | 10 | Y,B |
| 44 | 3% ABDA (0.14M) continuous | 1% PTSA | 1 | 7.0 | 7.1 | 9 | 8 | Y |
|  |  | 1% $NH_4Cl$ | 1 | ∞ | 18 | 100 | 17 | LY |
| 45 | 1.2% AEP | — | 2 | ∞ | 2.5 | 100 | 86 | LY |

TABLE 1B-continued

Vinyl Acetate/Butyl Acrylate Emulsion Polymers

| Example | X-Linker (molarity) | Catalyst | Oven[5] | Swell Index (DMF) 3 min cure[1] | 10 min cure[1] | % DMF Solubles 3 min | 10 min | color[2] |
|---|---|---|---|---|---|---|---|---|
|  | (0.076M) | 1% PTSA | 2 | 7.6 | 7.2 | 14 | 12 | DB |
|  | 1.0% AM (0.153M) continuous | 1% PTSA + 1% PVOH | 2 | 7.6 | 7.7 | 12 | 13 | DB |
| 46 | 3% DBMA | 2% PTSA | 2 | ∞ | ∞ | 100 | 100 | DY |
|  | (0.13M) continuous | 2% PTSA + 1% PVOH | 2 | ∞ | ∞ | 100 | 100 | DT |

TABLE 2

| Sample | X-Linker (molarity) | Catalyst | Oven[5] | Swell Index (DMF) 3 min cure | 10 min cure[1] | % DMF Solubles 3 min | 10 min | color[2] |
|---|---|---|---|---|---|---|---|---|
| 47 | 2.5% ADBC (0.1M) continuous | 1% PTSA | 2 | 5.4 | 4.9 | 10 | 10 | DB |
|  |  | 2% NH4Cl (0.38M) | 1 | ∞ | ∞ | 100 | 100 | LY |
| 48 | 5% AHP (0.21M) cont. (NH3) | 2% PTSA | 1 | 4.4 | 4.7 | 10 | 8 | Y |
|  |  | 2% NH4Cl (0.38M) | 1 | 5.6 | 4.9 | 22 | 20 | LY,Br[10] |
| 49 | 10% ABDA (0.47M) + 1% DCPA | 2% PTSA | 1 | 2.3 | 2.3 | 11 | 10 | DY |
|  |  | 2% NH4Cl (0.38M) | 1 | 3.7 | 3.1 | 13 | 10 | Y |

EXAMPLES 50-64

Solution Polymerizations

Table 3 sets forth solution polymerization data. Examples 50-64 were prepared by the following method: All of the solution polymerizations were run with 0.297 mmol comonomer per calculated g of polymer solids premixed with the other monomer(s).

| Charge |
|---|
| X g comonomer |
| (50-X) g butyl acrylate (BA) |
| 120 g dry toluene |
| 0.15 g 2,2'-azobisisobutyronitrile (AIBN) |

The first three components were mixed at room temperature and heated at 65° C. in a 250 mL round bottom flask with a magnetic stirring bar, reflux condenser and N2 blanket. The AIBN was then added to start the reaction. Monitoring of the unreacted free monomer (butyl acrylate and comonomer) was done by GC.

| Retention Times (min) | |
|---|---|
| butyl acrylate | 2.90 |
| ABDA | 8.16 |
| AADMA | 6.07 |
| AEP | 6.51 |
| AGDA | 6.26 |
| vinyl acetate | 0.88 |
| ADBC | 8.35 |
| Et-ABDA | 8.62 |
| N—(isobutoxymethyl)acrylamide (BNMA) | 5.94 |

In all but Example 51, additional 10 mg amounts of AIBN were added at random times to keep the reaction going. The temperature was also increased to 75° C. when the reaction rate decreased. Most of the reactions took longer than 24 hours, with Example 64 taking 107 hours. The reactions were terminated when the free monomer fell below 0.7%. Example 61 was run half scale.

TABLE 3

Solution Polymers

| Example | X-linker Comonomer (Molarity) | Catalyst/Additives | Oven[5] | Swell Index[1] (DMF) 3 min cure | 10 min cure | % DMF Solubles 3 min | 10 min | Color[2] | Tack[3] |
|---|---|---|---|---|---|---|---|---|---|
| 50 | — | 1% Thermal | 1 | ∞ | ∞ | 100 | 100 | — | — |
| 51 | BNMA (0.3M) | 1% Thermal | 1 | 2.5 | 2.1 | 5 | 11 | — | — |
| 52 | ABDA (0.3M) | 1% Thermal | 1 | 2.7 | 1.8 | 41[x] | 39[x] | — | — |
|  |  | 1% Thermal | 1 | 1.9 | 2.0 | 3 | 9 | — | — |
| 53 | AEP (0.3M) | 1% Thermal | 1 | 2.5 | 2.3 | 10 | 1 | — | — |
| 54 | AEP (0.6M) | — | 1 | 3.9 | 3.0 | 9 | 5 | 0 | ST |
|  |  | 1% Thermal | 1 | 2.2 | 1.9 | 13 | 12 | LY | ST |
| 55 | AEP (0.3M) +HEA (0.3M) | — | 1 | 3.4 | 3.1 | 7.2 | 6.7 | C | T |
|  |  | 1% Thermal | 1 | 2.5 | 2.4 | 18 | 12 | LY | ST |
| 56 | AEP (0.3M) +GAE (0.3M) | — | 1 | 3.9 | 3.9 | 22 | 13 | C | T |
|  |  | 1% Thermal | 1 | 2.6 | 2.6 | 17 | 12 | LY | N |
| 57 | AEP (0.05M) | — | 1 | ∞ | ∞ | 100 | 100 | C | VT |
|  |  | 1% Thermal | 1 | ∞ | ∞ | 100 | 100 | LY | T |
| 58 | AEP (0.1M) | — | 1 | ∞ | ∞ | 100 | 100 | C | VT |
|  |  | 1% Thermal | 1 | 2.3 | 2.2 | 14 | 6 | LY | T |
| 59 | AEP (0.05M) | — | 1 | ∞ | ∞ | 100 | 100 | C | VT |

TABLE 3-continued

Solution Polymers

| Example | X-linker Comonomer (Molarity) | Catalyst/ Additives | Oven[5] | Swell Index[1] (DMF) 3 min cure | Swell Index[1] (DMF) 10 min cure | % DMF Solubles 3 min | % DMF Solubles 10 min | Color[2] | Tack[3] |
|---|---|---|---|---|---|---|---|---|---|
|  | +HEA (0.05M) | 1% Thermal | 1 | 3.5 | 2.8 | 13 | 19 | LY | T |
| 60 | AEP (0.05M) | — | 2 | ∞ | ∞ | 100 | 100 | C | T |
|  | +AM (0.1M) | 1% Thermal | 2 | 3.6 | 3.8 | 16 | 12 | LY | T |
| 61 | Et-ABDA (0.3M) | 1% Thermal | 1 | ∞ | 4.2 | 100 | 27 | Y,DY | VT |
| 62 | AADMA (0.3M) | 1% Thermal | 1 | ∞ | 15.4 | 100 | — |  |  |
| 63 | AGDA (0.3M) | 1% Thermal | 1 | ∞ | 3.4 | 100 | 4 |  |  |
| 64* | ABDA | 1% Thermal | 1 | 1.7 | 1.9 | 56 | 46 | Y,DY | N |

*80.5% VAc, 13.1% BA, 6.4% ABDA

EXAMPLES 65-82

In Examples 65-82 polymers containing copolymerized acetal and hemiamidal monomers of the invention were applied as binder emulsions on Whatman paper at 10% binder solids add-on. Ammonium chloride was added as a curing catalyst at 1% on solids and the impregnated paper was dried and cured at 150° C. for 3 minutes. Table 4 shows the tensile strength values for the bonded paper.

TABLE 4

| Example | BASIC Polymer | Crosslinker Monomer | Addition Mode X-Linker Monomer | TENSILE VALUES (pli)[+] Dry | Wet | Perchloro | MEK |
|---|---|---|---|---|---|---|---|
| Paper without binder | — | — |  | 8.2 | 0.2 | 6.0 | — |
| VAc/Et |  | 0% |  | 12.5 | 1.0 | 3.5 | — |
| 65 | VAc/BA | 10% AEP | Trail | 11.6 | 3.4 | 4.4 | 3.4 |
| 66 | VAc/Ba | 10% AEP | Continuous | 15.5 | 6.0 | 7.2 | 5.4 |
| 67 | VAc/BA | 10% ABDA | Trail | 16.7 | 7.5 | 7.0 | 5.6 |
| 68 | VAc/BA | 7% ABDA | Trail | 10.9 | 4.0 | 5.3 | 3.9 |
| 69 | BA/MMA | 10% ABDA | Batch | 16.3 | 7.4 | 8.8 | 7.3 |
| 70 | VAc | 6% DBMA | Continuous | 7.3 | 1.4 | 5.4 | 3.3 |
| 71 | VAc | 10% DBMA | Trail | 14.3 | 2.2 | 7.1 | 2.6 |
| 72 | VAc | 3% DEBMU | Trail | 17.3 | 5.0 | 6.4 | 4.2 |
| 73 | VAc | 3% DEEMU | Trail | 17.3 | 6.3 | 7.1 | 4.1 |
| 74 | VAc/BA | 5% ABDA | Trail | 18.2 | 7.1 | 6.3 | 4.9 |
| 75 | VAc | 3% ABDA | Continuous | 17.1 | 5.5 | 8.4 | 3.6 |
| 76 | VAc | 5% ABMA | Continuous | 17.6 | 5.3 | — | 4.7 |
| 77 | VAc | 5% ABMA + 19% PVOH | Continuous | 19.9 | 4.5 | 11.5 | 5.7 |
| 78 | VAc | 6% APDA | Continuous | 13.0 | 3.3 | 6.9 | 4.5 |
| 79 | VAc | 2.5% ADEEU | Continuous | 16.2 | 4.6 | 6.1 | 3.0 |
| 80 | VAc | 5% DBVC | Continuous | 17.5 | 5.8 | 6.9 | 3.9 |
| 81 | VAc | 5% CBDA | Continuous | 17.3 | 5.0 | 7.2 | 4.3 |
| 82 | VAc | 4% VSEP | Continuous | 18.5 | 5.4 | 7.2 | 3.6 |

[+]On Whatman 3% paper, 10% add-on
Batch - crosslinker monomer added all up front to polymerization reaction.
Continuous - crosslinker monomer added continuously during polymerization reaction.
Trail - crosslinker monomer added continuously during last half of polymerization reaction.

| | |
|---|---|
| A-105 | Airflex 105 vinyl acetate/ethylene copolymer emulsion |
| BNMA | butoxymethylacrylamide |
| ABDA | acrylamidobutyraldehyde diethyl acetal |
| AEP | N—acrylamido-5-ethoxypyrrolidine |
| HEA | hydroxyethyl acrylate |
| GAE | glyceryl allyl ether |
| AM | acrylamide |
| AADMA | acrylamidoacetaldehyde dimethyl acetal |
| AGDA | N—allylglyoxylamide dimethyl acetal |
| HEMA | 2-hydroxyethylmaleamic acid |
| ADBC | O—allyl-N(4,4-diethoxybutyl)carbamate |
| x | anomalous result due to undersized sample |
| 1 | Cure at 150° C. |
| 2 | Colorless, (Light/Dark) Yellow, Brown |
| 3 | (Slightly/Very) Tacky, Not tacky |
| 4 | Oven 2 at 380° F. |
| 5 | Oven 1 - forced draft, Oven 2 - non-forced draft |
| 6 | cont = continuous comonomer addition; end = comonomer added at end of polymerization (core/shell system) |
| Thermal | cyclohexanol-2-p-toluenesulfonate, organic soluble thermally activated catalyst |
| PE | pentaerythritol |
| PEDA | pentaerythritol diacetonide |

| | |
|---|---|
| PTSA | p-toluenesulfonic acid |
| APTS | ammonium p-toluenesulfonate |
| MF | melamine/formaldehyde resin (Cymel 303) |
| IR | Irganox antioxidant, 500 ppm |
| TRIS | tris(hydroxymethyl)methylamine |
| VACOL-A | 35% hydrolysis PVOH |
| DBMA | diethoxybutylmaleamic acid |
| AHP | N—acryloyl-2-hydroxypyrrolidine |
| DCPA | dicyclopentadienyl acrylate |
| DEBMU | N—(diethoxybutyl)-N'—acryloxyethyl urea |
| DEEMU | N—(diethoxyethyl)-N'—acryloxyethyl urea |
| ABDA-Me | acrylamidobutyraldehyde dimethyl acetal |
| ADPA | acrylamidopentanal diethyl acetal |
| ADEEU | N—allyl-N'—(diethoxyethyl) urea |
| DBVC | N—(diethoxybutyl)-O—vinylcarbamate |
| CBDA | crotonamidobutyraldehyde diethyl acetal |

EXAMPLE 83

Homopolymerization of AEP

AEP (50 g) was mixed with 100 g of isopropanol, 0.3 g of tetradecane (as internal standard) and 50 mg of azobisisobutyronitrile (AIBN) and heated at 67° C. under nitrogen. Gas chromatographic analysis showed 53% conversion after 4 h and 99.7% after 23 h. The product was a viscous solution, 67% solids (due to isopropanol evaporation).

EXAMPLE 84

1:1 Copolymerization of AEP with Butyl Acrylate

A mixture of 25 g each of butyl acrylate with AEP, 100 g of isopropanol, 0.3 g of tetradecane and 50 mg of AIBN was reacted as in Example 83. GC monitoring showed similar reactivity for the two monomers with 99 and 99.4% conversion respectively after overnight heating.

EXAMPLE 85

Styrene/ABDA (95/5) Emulsion Copolymer Synthesis

A 2 L reactor was charged with 590 g of deionized water, 26.7 g of Steol CS-130, 17.0 g of Igepal CO-850 and 0.8 g of methacrylic acid. The reactor was purged with nitrogen for 30 min. The kettle was heated to 40° C., 126.7 g of styrene and 6.7 g of ABDA were added, and the contents of the reactor were stirred for 15 min. Then 2.0 g of ammonium persulfate was added and 100 g of a 1% aqueous solution of SFS was added at 0.34 mL/min. Initiation occurred 2 min after beginning the activator delay. Fifteen min later a solution of 253.3 g of styrene and 13.3 g of ABDA was added at 2.84 mL/mn. Following complete monomer addition, the kettle was heated to 90° C. and treated with 5 drops of tBHP. Twenty min later the reaction was over.

EXAMPLE 86

Styrene/N-(4,4-Diethoxybutyl)cinnamide (DEBC)(95/5) Emulsion Copolymer

Same as Example 85 except DEBC was used instead of ABDA, and initiation required 2.5 min.

STATEMENT OF INDUSTRIAL APPLICATION

The invention provides self- and hydroxyl reactive, formaldehyde-free cyclic hemiamidal and hemiamide ketal crosslinking monomers and their derived polymers suitable as binders for nonwoven products.

We claim:

1. A compound represented by the following formula:

$$R-N\underset{R^2O}{\overset{(CH_2)_n}{\diagdown C \diagup}} R^4$$

wherein R is an olefinically unsaturated organic radical represented by one of the following formulas $$R^5-\overset{O}{\underset{\|}{C}}- \quad (a)$$

where $R^5$ is a $C_2$–$C_{23}$ organic radical of the formula $$X\!\!-\!\!=\!\!<\!\!\genfrac{}{}{0pt}{}{Z}{(Y)_{\overline{m}}}$$

where
X is hydrogen, $C_1$–$C_{10}$ alkyl, phenyl, —C(O)NH$_2$, or —CO$_2$R$^8$ where R$^8$ is hydrogen or a $C_1$–$C_9$ alkyl group,
Y is —O—, —CH$_2$O—, —NR$^6$—, —CH$_2$NR$^6$—, —(CO)—O—(CH$_2$)$_a$—NR$^6$—, where R$^6$ is hydrogen or a $C_1$–$C_4$ alkyl radical and a is 1 to 4, —O(CO)—, —N(CO)—, a branched or unbranched $C_1$ to $C_8$ alkylene group, or —C$_6$H$_4$—,
Z is hydrogen, $C_1$–$C_4$ alkyl, —C(O)NH$_2$, —CO$_2$R$^7$ where R$^7$ is hydrogen or a $C_1$–$C_3$ alkyl group,
m is 0 or 1;

$$R^5\diagdown\!\!\underset{N}{\overset{N}{\diagup}}\!\!\diagdown\!\!\underset{Q}{\overset{N}{\diagup}} \quad (b)$$

where $R^5$ is as defined above, Q is hydrogen, hydroxy, $C_1$–$C_4$ alkoxy or alkylamino, $$-NH-(CH_2)_n-\overset{OR^2}{\underset{OR^3}{\overset{|}{\underset{|}{C}}R^4}} \text{ or } -N\underset{R^2O}{\overset{(CH_2)_n}{\diagdown C \diagup}} R^4$$

-continued
$$CH_2=CH-SO_2H \quad (c)$$

where
$R^2$ is hydrogen or a $C_1-C_4$ alkyl group,
$R^4$ is hydrogen or a $C_1-C_4$ alkyl group, and
n is 3.

2. The compound of claim 1 in which $R^4$ is hydrogen.

3. The compound of claim 1 in which $R^2$ is methyl or ethyl.

4. A compound of claim 1 in which R is $R^5$—C(O)— and $R^5$ is as defined.

5. The compound of claim 4 in which the olefinically unsaturated acyl radical is a $C_3-C_{10}$ alpha,beta unsaturated alkenoyl radical.

6. The compound of claim 5 in which the acrylyl radical is an acryloyl.

7. The compound of claim 1 in which R is

<chemical structure: triazine ring with $R^5$ and Q substituents> and $R^5$ and q are as defined.

8. The compound of claim 1 in which R is $CH_2=CH-SO_2-$.

9. A compound represented by the following formula:

<chemical structure: R-N with (CH2)n ring, $R^2O$ and H on C> wherein R is an olefinically unsaturated organic radical represented by the following formula $$R^5-\overset{O}{\underset{\|}{C}}-$$

where $R^5$ is a $C_2-C_{23}$ organic radical of the formula $$\text{\large{*}}=\mathrel{\mathop{<}^{Z}_{(Y)_{\overline{m}}}}$$

where
X is hydrogen, $C_1-C_{10}$ alkyl, phenyl, —C(O)NH₂, —CO₂R⁸ where R⁸ is hydrogen or a $C_1-C_9$ alkyl group,
Y is —O—, —CH₂O—, —NR⁶—, —CH₂NR⁶—; —(CO)—O—(CH₂)ₐ—NR⁶—, where R⁶ is hydrogen or a $C_1-C_4$ alkyl radical and a is 1 to 4, —O(-CO)—, —N(CO)—, a branched or unbranched $C_1$ to $C_8$ alkylene group, or —C₆H₄—;
Z is hydrogen, $C_1-C_4$ alkyl, —C(O)NH₂, —CO₂R⁷ where R⁷ is hydrogen or a $C_1-C_3$ alkyl group,
m is 0 or 1,
$R^2$ is a $C_1-C_4$ alkyl group, and
n is 3.

10. The compound of claim 9 in which the olefinically unsaturated acyl radical is a $C_3-C_{10}$ alpha,beta unsaturated alkenoyl radical.

11. The compound of claim 10 in which the alkenoyl radical is acrylyl or methacrylyl.

12. The compound of claim 9 in which $R^2$ is methyl or ethyl.

13. The compound of claim 10 in which $R^2$ is methyl or ethyl.

14. The compound of claim 7 in which $R^2$ is methyl or ethyl.

15. A compound represented by the formula

<chemical structure: $R^5-C(=O)-N$ with $(CH_2)_n$ ring, $R^2O$ and H on C> wherein $R^2$ is a $C_1-C_4$ alkyl radical, $R^5$ is a $C_3-C_{10}$ alkenoyl radical, and n is 3.

16. The compound of claim 15 in which the alkenoyl radical is acrylyl or methacrylyl.

17. The compound of claim 16 in which $R^2$ is methyl or ethyl.

18. A compound of the formula

<chemical structure: $CH_2=CH-C(=O)-N$ with $(CH_2)_3$ ring, RO and H on C> where R is methyl or ethyl.

19. A compound of the formula

<chemical structure: $CH_2=CH-CH_2-O-C(=O)-N$ with $(CH_2)_3$ ring, RO and H on C> where R is methyl or ethyl.

20. A compound of the formula

<chemical structure: $CH_2=C(CH_3)-C(=O)-O-(CH_2)_2-NH-C(=O)-N$ with $(CH_2)_3$ ring, RO and H on C> where R is methyl or ethyl.

21. A compound of the formula

<chemical structure: $RO-C(=O)-CH=CH-C(=O)-N$ with $(CH_2)_3$ ring, RO and H on C> where R is methyl or ethyl.

* * * * *